(12) United States Patent
Los et al.

(10) Patent No.: US 10,077,435 B2
(45) Date of Patent: *Sep. 18, 2018

(54) HOST CELL CAPABLE OF PRODUCING ENZYMES USEFUL FOR DEGRADATION OF LIGNOCELLULOSIC MATERIAL

(71) Applicant: DSM IP ASSETS B.V., Heerlen (NL)

(72) Inventors: Alrik Pieter Los, Echt (NL); Cornelis Maria Jacobus Sagt, Echt (NL); Margot Elisabeth Francoise Schooneveld-Bergmans, Echt (NL); Robbertus Antonius Damveld, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,967

(22) Filed: Dec. 21, 2016

(65) Prior Publication Data

US 2017/0114337 A1    Apr. 27, 2017

Related U.S. Application Data

(60) Continuation of application No. 14/793,786, filed on Jul. 8, 2015, now Pat. No. 9,738,881, which is a division of application No. 13/578,152, filed as application No. PCT/EP2011/052059 on Feb. 11, 2011, now Pat. No. 9,109,214.

(30) Foreign Application Priority Data

Feb. 11, 2010 (EP) ..................... 10153353

(51) Int. Cl.
    C12P 7/06     (2006.01)
    C12N 9/42     (2006.01)
    C12P 19/14    (2006.01)
    C12P 19/02    (2006.01)

(52) U.S. Cl.
    CPC ........... *C12N 9/2437* (2013.01); *C12N 9/244* (2013.01); *C12N 9/2445* (2013.01); *C12P 19/02* (2013.01); *C12P 19/14* (2013.01); *C12Y 302/01006* (2013.01); *C12Y 302/01021* (2013.01); *C12Y 302/01091* (2013.01)

(58) Field of Classification Search
    CPC .... C12Y 302/01021; C12Y 302/01091; C12N 9/2445
    USPC ...................................................... 435/252.3
    See application file for complete search history.

(56) References Cited

U.S. PATENT DOCUMENTS

| 9,109,214 | B2* | 8/2015 | Los | ............... | C12P 19/14 |
| 9,738,881 | B2* | 8/2017 | Los | ............... | C12N 9/2437 |
| 2006/0127976 | A1 | 6/2006 | Wenzel et al. | | |
| 2015/0329843 | A1 | 11/2015 | Los et al. | | |

FOREIGN PATENT DOCUMENTS

| WO | 2001070998 | A2 | 9/2001 |
| WO | 2004070022 | A2 | 8/2004 |
| WO | 2007091231 | A1 | 8/2007 |
| WO | 2008153903 | A2 | 12/2008 |
| WO | 2011054899 | | 5/2011 |

OTHER PUBLICATIONS

International Search Report for PCT/EP2011/052059 dated Apr. 29, 2011.
Penttila, "Construction and Characterization of Cellulolytic Yeasts," Database Biosis [Online], Bioscience Information Service, Database Accession No. PREV198885067522, (1987).
Petersen et al., "Development of a Polysaccharide Degrading Strain of *Saccharomyces cerevisiae*," Biotechnology Techniques, vol. 12, No. 8, pp. 615-619, (Aug. 1998).
Gao et al., "Mixture Optimization of Six Core Glycosyl Hydrolases for Maximizing Saccharification of Ammonia Fiber Expansion (AFEX) Pretreated Corn Stover," Bioresources Technology, vol. 101, No. 8, pp. 2770-2781, (Nov. 30, 2009).
Accession Nos. (AC) Q8TFL9 (95.7% identical to SEQ ID No: 1); AC Q8WZD7 (94.1% identical to SEQ ID No: 3); AC Q8TGI8 (100% identical to SEQ ID No: 5); and AC Q8NIB5 (91% identical to SEQ ID No: 7) (2002).
Penttilä, Merja, "Construction and characterization of cellulolytic yeasts." Technical Research Centre of Finland Valtion Teknillinen Tutkimuskeskus ESPOO (1987).
Kumar et al., "Methods for Pretreatment of Lignocellulosic Biomass for Efficient Hydrolysis and Biofuel Production." Ind. Eng. Chem. Res. 2009, 48:08, 3713-3729.
J.W.A. Langeveld et al., "Development Perspectives of the Biobased Economy: A Review." Crop Science, vol. 50, Mar.-Apr. 2010.
Murray et al., "Expression in Trichoderma reesei and characterisation of a thermostable family 3 -glucosidase from the moderately thermophilic fungus Talaromyces emersonii." Protein Expression and Purification 38 (2004) 248-257.

(Continued)

*Primary Examiner* — Tekchand Saidha
(74) *Attorney, Agent, or Firm* — McBee Moore Woodward & Vanik IP, LLC; Susan McBee; Chester Moore

(57) ABSTRACT

The invention relates to a host cell comprising at least four different heterologous polynucleotides chosen from the group of polynucleotides encoding cellulases, hemicellulases and pectinases, wherein the host cell is capable of producing the at least four different enzymes chosen from the group of cellulases, hemicellulases and pectinases, wherein the host cell is a filamentous fungus and is capable of secretion of the at least four different enzymes. This host cell can suitably be used for the production of an enzyme composition that can be used in a process for the saccharification of cellulosic material.

22 Claims, 5 Drawing Sheets

Specification includes a Sequence Listing.

(56) References Cited

OTHER PUBLICATIONS

International Search Report dated Feb. 3, 2016, issued in EP 11 703 000.7.

\* cited by examiner

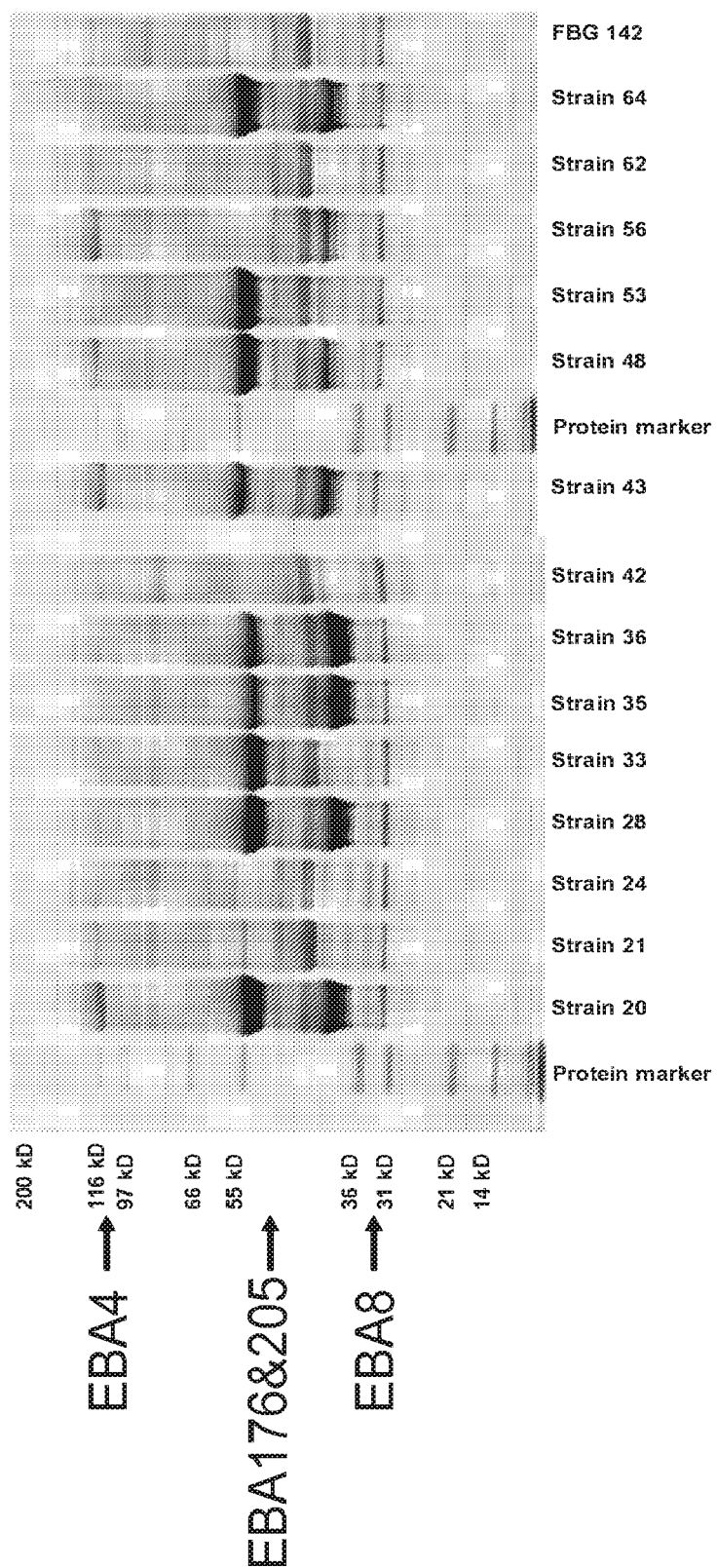

HOST CELL CAPABLE OF PRODUCING ENZYMES USEFUL FOR DEGRADATION OF LIGNOCELLULOSIC MATERIAL

CROSS REFERENCE TO RELATED APPLICATIONS

This application is a continuation of U.S. Ser. No. 14/793,786, filed Jul. 8, 2015, which is a divisional of U.S. Ser. No. 13/578,152, filed Oct. 24, 2012, which is a 371 of PCT/EP2011/052059, filed Feb. 11, 2011, which claims priority to EP 10153353.7, filed Feb. 11, 2010, the contents of which are incorporated herein by reference in their entireties.

STATEMENT OF FEDERALLY SPONSORED RESEARCH AND DEVELOPMENT

This invention was made with US Government support under Grant No. DE-FC36-08G018079, awarded by the Department of Energy. The US Government may have certain rights in this invention.

REFERENCE TO SEQUENCE LISTING SUBMITTED AS A COMPLIANT ASCII TEXT FILE (.txt)

A Sequence Listing is submitted herewith as an ASCII compliant text file named "2919208-198001_Sequence_listing.txt"), created on Jun. 23, 2015, and having a size of 48,485 bytes as permitted under 37 C.F.R. § 1,821(c). The material in the aforementioned file is hereby incorporated by reference in its entirety.

BACKGROUND OF THE INVENTION

Field of the Invention

The invention relates to a host cell capable of producing at least four different enzymes chosen from the group of cellulases, hemicellulases and pectinases, a process for the preparation of said host cell, an enzyme composition produced by said host cell, a process for the production of an enzyme composition using said host cell, a process for the saccharification of lignacellulosic material using the enzyme composition and a process for the preparation of a fermentation product using the enzyme composition.

Description of Related Art

Carbohydrates constitute the most abundant organic compounds on earth. However, much of this carbohydrate is sequestered in complex polymers including starch (the principle storage carbohydrate in seeds and grain), and a collection of carbohydrates and lignins known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks.

The sequestration of large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, and fuels.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain.

With productivity of a strain is meant the amount of total protein or enzyme activity produced in the fermentation broth per time, for example kg protein/($m^3$ broth·year) or enzyme units/($m^3$ broth·year).

An enzyme unit is the ability of a defined amount of protein to convert a defined substrate under certain defined conditions.

SUMMARY

The presence of a separate 'cellulase inducer' is usually needed to produce the enzymes for biomass conversion in a microorganism. A cellulase inducer is disadvantageous for the following reasons. First, the inducer, such as a plant material, may have a variable composition, which is disadvantageous for the controllability of the expression of the heterologous polynucleotides chosen from the group of polynucleotides encoding cellulases, hemicellulases and pectinases. Secondly, energy is required to sterilise plant material before the inducer can be used for inducing the production of the at least four different enzymes chosen from the group of cellulases, hemicellulase and pectinases. Thirdly, plant material will heavily pollute fermentation equipment. Fourthly, the inducer may result in a higher viscosity of the medium wherein the host cell expresses the at least four different polynucleotides chosen from the group of polynucleotides encoding celluloses, hemicellulases and pectinases. Fifthly, the presence of a 'cellulose inducer', in particular when it has been pre-treated, may result in the production of inhibitors that may be detrimental to the host cell.

"Cellulose inducer" is herein defined as a compound that induces the production of cellulose in the host cell. Examples of cellulose inducers include pure cellulose, cellobiose, sophorose and gentiobiose or any lignocellulosic material.

It would therefore be highly desirable to provide a simple and economically attractive enzymatic process for the production of sugars from plant biomass.

This object has been achieved by the provision of a host cell comprising at least four different heterologous polynucleotides chosen from the group of polynucleotides encoding cellulases, hemicellulases and pectinases, wherein the host cell is capable of producing the at least four different enzymes chosen from the group of celluloses, hemicellulases and pectinases, wherein the host cell is a filamentous fungus and is capable of secretion of the at least four different enzymes Since all enzymes necessary for degradation of lignocellulosic material are produced in and secreted by one and the same host cell, a ready-to-use enzyme composition can be produced in only one fermentation. The enzyme composition produced by the host cell of the invention can suitably be used in a process for the saccharification of lignocellulosic material.

Furthermore, the host cell of the invention may not need a cellulose inducer to produce the at least four different enzymes chosen from the group of celluloses, hemicellulases and pectinases.

A possible advantage of using the host cell of the invention in a process for the saccharification of lignocellulosic material is that it is not necessary to blend/mix the enzymes needed for the degradation of the lignocellulosic material in the desired ratios. Furthermore, there is no need to store separate enzymes before using them in a process for the degradation of lignocellulosic material.

Furthermore, by selecting the host cell and the genetic modifications of the host cell according to the preferred embodiments of the invention, a high productivity of the enzymes can be achieved.

Furthermore, the fermentation broth (comprising the at least four different enzymes chosen from the group of celluloses, hemicellulases and pectinases) may be used without any purification in a process for the degradation of lignocellulosic material. Therefore, the invention provides a very simple and cost-effective solution.

BRIEF DESCRIPTION OF THE DRAWINGS

FIGS. 4A-4B: Detection of multiple recombinant *T. emersonii* cellulases in *T. emersonii*.

Figure 1:
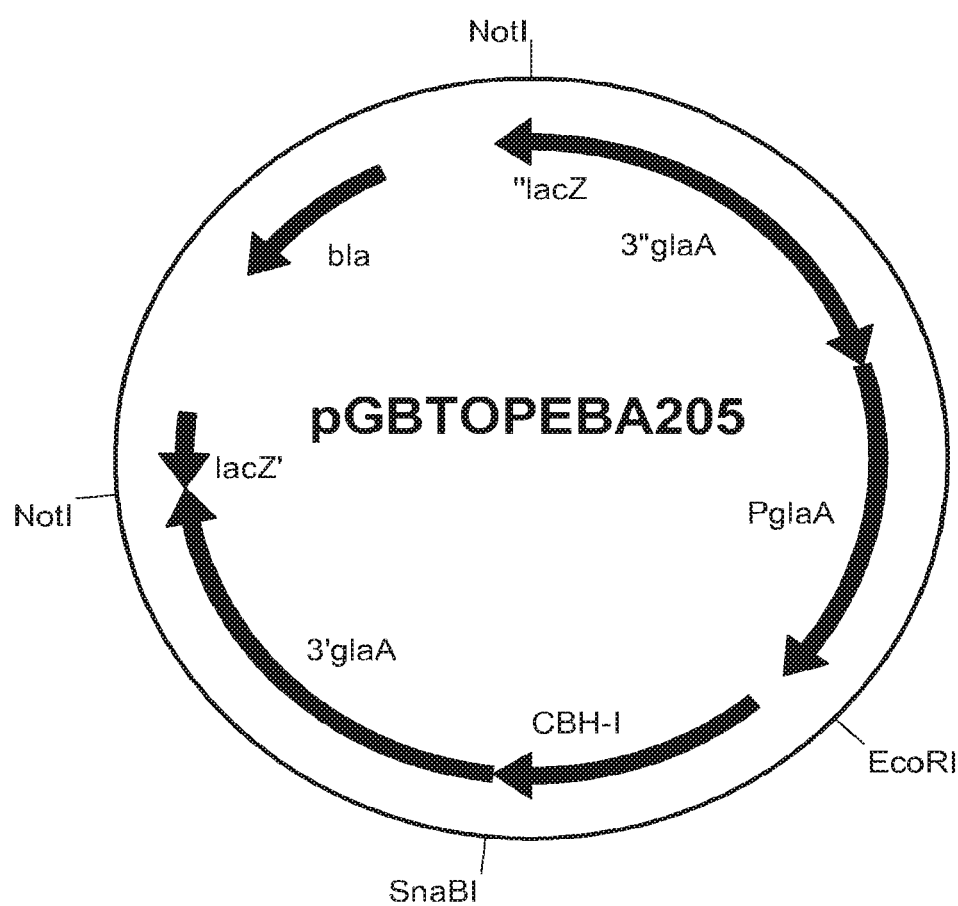
FIG. 1: Map of pGBTOPEBA205 for expression of *T. emersonii* cellobiohydrolase I (CBH I) in *T. emersonii*. Depicted are EBA205 expressed from the glucoamylase promoter (PglaA). In addition, the glucoamylase flank (3'glaA) of the expression cassette is depicted. pGBTOPEBA205 is representative for pGBTOPEBA8, which comprises the DNA-sequence encoding the *T. emersonii* EG, and pGBTOPEBA4, which comprises DNA-sequence encoding the *T. emersonii* BG.

(4A). SDS-PAGE detection of *T. emersonii* cellulases expressed in *T. emersonii*. *T. emersonii* was transformed with a mix of pGBTOPEBA4, pGBTOPEBA8, pGBFINEBA176, and pGBTOPEBA205. Approximately 400 transformants were grown in 96-well plates and screened for expression of at least one cellulase by E-PAGE gel analysis. Interesting transformants were grown in shake flasks containing glucose-based medium and proteins in supernatants harvested from 72 hours cultures were TCA-precipitated and analysed by SDS-PAGE analysis. FBG142 is the empty strain.

(4B). Graph showing WSU activity in transformants. Transformants were grown for 72 hours in glucose-based medium and WSU activity was determined in 16-times diluted supernatants of the cultures. FBG142 is the empty strain.

BRIEF DESCRIPTION OF THE SEQUENCE LISTING

SEQ ID NO: 1 sets out the amino acid sequence of a cellobiohydrolase I from *Talaromyces emersonii*

SEQ ID NO: 2: sets out the polynucleotide from *Talaromyces emersonii* encoding the amino acid sequence of SEQ ID NO. 1.

SEQ ID NO: 3 sets out the amino acid sequence of a β-glucanase CEA from *Talaromyces emersonii*.

SEQ ID NO: 4 sets out the polynucleotide from *Talaromyces emersonii* encoding the amino acid sequence of SEQ ID NO. 3.

SEQ ID NO: 5 sets out the amino acid sequence of a δ-glucosidase from *Talaromyces emersonii*.

SEQ ID NO: 6 sets out the polynucleotide from *Talaromyces emersonii* encoding the amino acid sequence of SEQ ID NO. 5.

SEQ ID NO: 7 sets out the amino acid sequence of a cellobiohydrolase II from *Talaromyces emersonii*.

SEQ ID NO: 8 sets out the polynucleotide from *Talaromyces emersonii* encoding the amino acid sequence of SEQ ID NO. 7.

SEQ ID NO: 9 sets out the aminoacid sequence of a Size 209 aa unknown protein from *T. emersonii*.

SEQ ID NO: 10 sets out the coding sequence of an unknown protein from *T. emersonii* having aminoacid sequence according to SEQ ID NO: 9.

SEQ ID NO: 11 sets out the aminoacid sequence of *T. emersonii* swollenin.

SEQ ID NO: 12 sets out the coding sequence of *T. emersonii* swollenin.

SEQ ID NO: 13 sets out the aminoacid sequence of *T. emersonii* acetyl xylan esterase.

SEQ ID NO: 14 sets out the coding sequence of *T. emersonii* acetyl xylan esterase.

SEQ ID NO: 15 sets out the aminoacid sequence of *T. emersonii* xylanase.

SEQ ID NO: 16 sets out the coding sequence of *T. emersonii* xylanase.

DETAILED DESCRIPTION OF A PREFERRED EMBODIMENT

As used herein the expression "heterologous polynucleotides" means polynucleotides that are not present in the untransformed host cell, whereas "homologous polynucleotides" means polynucleotides that are present in the untransformed host cell. Synthetic polynucleotides are herein considered heterologous polynucleotides, independent of their potential presence in the untransformed host cell.

As used herein "transformant" means a cell that has been the object of transformation. "Transformant", "host cell" and "recombinant cell" are herein used as synonyms.

"Transformation" herein means the genetic alteration of a cell by means of recombinant technology. It may result in the uptake, incorporation, and expression of genetic material (DNA. RNA or protein) or mutation or deletion of genetic material in the cell, through human intervention.

The Host Cell

The host cell according to the invention may be prepared from any cell. For specific uses of a compound produced in a host cell according to the invention, the selection of the cell to be transformed may be made according to such use. Where e.g. the compound produced in a host cell according to the invention is to be used in food applications, a host cell may be selected from a food-grade organism such as *Saccharomyces cerevisiae*. Specific uses include, but are not limited to, food, (animal) feed, pharmaceutical, agricultural such as crop-protection, and/or personal care applications.

According to one embodiment, the host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6™ cells, and hybridomas. Preferred insect cells include e.g. Sf9 and Sf21 cells and derivatives thereof. More preferably, the eukaryotic cell is a fungal cell, i.e. a yeast cell, such as a *Candida, Hansenuta, Kluyverornyces, Pichia, Saccharomyces, Schizosaccharomyees*, or *Yarrowia* strain, more preferably from *Kluyverornyces lactis, S. cerevisiae. Hansenula polymorpha, Yarrowia lipolytica* and *Pichia pastoris*, or a filamentous fungal cell. Most preferably, the eukaryotic cell is a filamentous fungal cell.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium*, and *Trichoderma*.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

Preferred filamentous fungal cells belong to *Aspergillus, Chrysosporium, Penicillium, Talaromyces* of *Trichoderma* genus, and most preferably *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum*.

Most preferably, the cell to be transformed to form the host cell is an *Aspergillus*.

An advantage of expression of the enzymes (the at least four different cellulases, hemicellulases and/or pectinases) in *Aspergillus* may be a high enzyme yield on sugar.

When the cell to be transformed to form the host cell according to the invention is an *Aspergillus* strain, the *Aspergillus* strain is preferably CBS 513.88 or a derivative thereof, more preferably the host cell is *Aspergillus niger* CBS 513.88.

According to another embodiment, the cell to be transformed to form the host cell according to the invention is a prokaryotic cell. Preferably, the prokaryotic host cell is bacterial cell. The term "bacterial cell" includes both Gram-negative and Gram-positive microorganisms. Suitable bacteria may be selected from the group of *Escherichia, Anabaena, Caulobactert, Gluconobacter, Rhodobacter, Pseudomonas, Paracoccus, Brevibacterium, Corynebacterium, Rhizobium (Sinorhizobium), Flavobacterium, Klebsiella, Enterobacter, Lactobacillus, Lactococcus Methylobacterium Staphylococcus* and *Streptomyces*. Preferably, the bacterial cell is selected from the group of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter*.

The Enzymes

In the invention, the at least four different enzymes are chosen from the group of cellulases, hemicellulases and pectinases, preferably from the group of cellulases and hemicellulases and more preferably from the group of cellulases.

Cellulases are enzymes that hydrolyze cellulose (β-1,4-glucan or β D-glucosidic linkages) resulting in the formation of glucose, cellobiose, cellooligosaccharides, and the like.

Cellulases have been traditionally divided into three major classes: endoglucanases (EC 3.2.1.4) ("EG"), exoglucanases or cellobiohydrolases (EC 3.2.1.91) ("CBH") and β-glucosidases ([β]-D-glucoside glucohydrolase; EC 3.2.1.21) ("BG"). See e.g. Knowles et al., TIBTECH 5, 255-261, 1987; Shulein, Methods Enzymol., 160, 25, pp. 234-243, 1988. Endoglucanases act mainly on the amorphous parts of the cellulose fibre, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suurnakki, et al. Cellulose 7:189-209, 2000). β-glucosidase acts to liberate D-glucose units from cellobiose, cellooligosaccharides, and other glucosides (Freer, J. Biol. Chem. vol. 268, no. 13, pp. 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aubert et al., 1988; Wood et al., Methods in Enzymology, vol. 160, no. 9, pp. 87-116, 1988, and Coughlan, et al., "Comparative Biochemistry of Fungal and Bacterial Cellulolytic Enzyme Systems" Biochemistry and Genetics of Cellulose Degradation, pp. 11-30 1988.

Fungal cellulase classifications of CBH, EG and BG can be further expanded to include multiple components within each classification. For example, multiple CBHs. EGs and BGs have been isolated from a variety of fungal sources including *Trichoderma reesei* which contains known polynucleotides coding for 2 CBHs, i.e., CBH I and CBH II, at least 8 EGs, i.e., EG EG II, EG III, EGIV, EGV, EGVI, EGVII and EGVIII, and at least 5 BGs, i.e., BG1, BG2, BG3, BG4 and BG5.

Accordingly, an enzyme composition of the invention may comprise any cellulase, for example, a cellobiohydrolase, an endo-β-1,4-glucanase, a β-glucosidase or a β-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the non-reducing ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-β-glucanase. This type of enzyme hydrolyses 1,3- or 1,4-linkages in β-D-glucans when the glucose residue whose reducing group is involved in the linkage to be hydrolysed is itself substituted at C-3. Alternative names include endo-1,3-β-glucanase, laminarinase, 1,3-(1,3;1,4)-β-D-glucan 3 (4) glucanohydrolase; substrates include laminarin, lichenin and cereal β-D-glucans.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

The host cell may produce and secrete endoglucanase activity and/or cellobiohydrolase activity and/or β-glucosidase activity. The host cell may produce and secrete more than one enzyme activity in one or more of those classes. For example, the host cell may produce and secrete two endoglucanase activities, for example, endo-1,3(1,4)-β glucanase activity and endo-β-1,4-glucanase activity.

Herein, a hemicellulase is any polypeptide which is capable of degrading or modifying hemicellulose. That is to say, a hemicellulase may be capable of degrading or modifying one or more of xylan, araban, glucuronoxylan, arabinogalactan, arabinoxylan, glucomannan, galactomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase may give rise to a mixed population of oligosaccharides and sugar monomers when contacted with the hemicellulase. Such degradation will typically take place by way of a hydrolysis reaction.

A composition of the invention may comprise any hemicellulase, for example, an endoxylanase, a β-xylosidase, an α-L-arabinofuranosidase, an acetyl-xylan esterase, an α-D-glucuronidase, an cellobiohydrolase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative endoxylanase is EC 3.2.1.136, a glucuronoarabinoxylan endoxylanase, an enzyme that is able to hydrolyse 1.4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an β-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+$H_2O$→alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl-xylan esterase (EC 3.1.1.72) is any polypeptide which is capable of hydrolysis of specifically the ester linkages of the acetyl groups in positions 2 and/or 3 of the xylose moieties of natural xylan.

Herein, a feruloyl esterase (EC 3.1.1.73) is any polypeptide which is capable of catalyzing a reaction of the form: feruloyl-saccharide+$H_2O$→ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+$H_2O$→coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase. β-galactosidase is an enzyme that may accept as its substrate both hemicellulose and pectine, therefore it is classified as a hemicellulase and as a pectinase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosaccharides and sugar monomers when contacted with the pectinase. Such degradation will typically take place by way of a hydrolysis reaction.

A host cell according to the invention may comprise a heterologous polynucleotide encoding any pectinase, for example an endo polygalacturonase, a pectin methyl esterase, an endo-galactanase, a β-galactosidase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n $H_2O$→n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase. PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: (1,4-α-D-galacturonide)$_n$+ $H_2O$→(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin.

This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

An α-L-arabinofuranosidase may accept as its substrate both hemicellulose and pectine, therefore it is classified as both a hemicellulase and a pectinase.

Herein, an α-L-arabinofuranosidase (EC 3.2:1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

In a special embodiment of the invention, the at least four different enzymes are at least two different cellobiohydrolases, for example a cellobiohydrolase I and/or a cellobiohydrolase II, optionally at least an endoglucanase, for example β-gluconase CEA and at least a β-glucosidase.

Preferably, one of said different cellobiohydrolases has at least 70% identity with SEQ ID No. 1 and the other of said different cellobiohydrolases has at least 70% identity with SEQ ID No. 7, wherein the endoglucanase has at least 70% identity with SEQ ID No. 3 and wherein the β-glucosidase has at least 70% identity with SEQ ID No. 5.

For example, one cellobiohydrolase may have at least 75%, for example at least 80%, for example at least 85%, for example at least 90%, for example at least 93%, for example at least 95%, for example at least 97%, for example at least 98%, for example at least 99% identity with SEQ ID NO. 1.

For example, the other cellobiohydrolase may have at least 75%, for example at least 80%, for example at least 85%, for example at least 90%, for example at least 93%, for example at least 95%, for example at least 97%, for example at least 98%, for example at least 99% identity with SEQ ID NO. 7.

For example, the endoglucanase may have at least 75%, for example at least 80%, for example at least 85%, for example at least 90%, for example at least 93%, for example at least 95%, for example at least 97%, for example at least 98%, for example at least 99% identity with SEQ ID NO. 3.

For example, the β-glucosidase may have at least 75%, for example at least 80%, for example at least 85%, for example at least 90%, for example at least 93%, for example at least 95%, for example at least 97%, for example at least 98%, for example at least 99% identity with SEQ ID NO. 5.

Preferably, the enzymes produced by the host cell of the invention have a cellulase activity of at least 2 WSU in 16 times or more diluted supernatant or broth, for example a cellulase activity of at least 3 WSU or a cellulase activity of at least 5 WSU or more in 16 times diluted supernatant or broth. The broth or supernatant may for example be 10000 times diluted, 5000 times diluted or 2500 times diluted.

With 1 WSU is meant 0.119 mg/ml glucose released from 2.1 w/v % washed pre-treated wheat straw by 200 µl of enzyme mix in 20 hours at 65° C. at pH 4.50.

When the heterologous cellulase, hemicellulase and/or pectinase is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a protein native to the host cell can be used. Preferably, said native protein is a highly secreted protein, i.e. a protein that is secreted in amounts higher than 10% of the total amount of protein being secreted.

As an alternative for a signal sequence, the polypeptide of the invention can be fused to a secreted carrier protein, or part thereof. Such chimeric construct is directed to the secretion route by means of the signal sequence of the carrier protein, or part thereof. In addition, the carrier protein will provide a stabilizing effect to the polypeptide according to the invention and or may enhance solubility. Such carrier protein may be any protein. Preferably, a highly secreted protein is used as a carrier protein. The carrier protein may be native or foreign to the polypeptide according to the invention. The carrier protein may be native of may be foreign to the host cell. Examples of such carrier proteins are glucoamylase, prepro sequence of alpha-Mating factor, cellulose binding domain of *Clostridium cellulovorans* cellulose binding protein A, glutathione S-transferase, chitin binding domain of *Bacillus circulans* chitinase A1, maltose binding domain encoded by the malE gene of *E. coli* K12, beta-galactosidase, and alkaline phosphatase. A preferred carrier protein for expression of such chimeric construct in *Aspergillus* cells is glucoamylase.

The Polynucleotides

The term "polynucleotide" is identical to the term "nucleic acid molecule" and can herein be read interchangeably. The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell. The polynucleotide may be synthetic or may be isolated from chromosomal DNA.

As used herein, the term "gene" refers to nucleic acid molecules, which may be isolated from chromosomal DNA or may be synthesized based on a sequence listing, which includes an open reading frame encoding a polypeptide.

The polynucleotide according to the invention may be a synthetic polynucleotide. The synthetic polynucleotide may be optimized in its codon use, preferably according to the methods described in WO2006/077258 and/or PCT/EP2007/055943, which are herein incorporated by reference. PCT/EP2007/055943 addresses codon-pair optimization. Codon-pair optimisation is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

The term "coding sequence" as defined herein is a sequence, which is transcribed into mRNA and translated into a polypeptide according to the invention. The boundaries of the coding sequence are generally determined by the ATG or other start codon at the 5'-end of the mRNA and a translation stop codon sequence terminating the open reading frame at the 3'-end of the mRNA. A coding sequence can include, but is not limited to, DNA, cDNA, and recombinant nucleic acid sequences.

The at least four different heterologous polynucleotides encoding the enzymes chosen from the group of cellulases, hemicellulases and pectinases can be chosen from any of the known polynucleotides.

Preferably, the polynucleotide is chosen from the group of polynucleotides encoding cellulases, hemicellulases and pectinases, is chosen from the group of polynucleotides encoding cellulases and hemicellulases, more preferably from the group of polynucleotides encoding cellulases.

In an embodiment, a polynucleotide according to the invention is chosen from the polynucleotides that encode a thermostable enzyme. Herein, this means that the enzyme has a temperature optimum of about 60° C. or higher, for example about 70° C. or higher, such as about 75° C. or higher, for example about 80° C. or higher such as 85° C. or higher. The skilled person may select suitable polynucleotides using common knowledge. They may for example be isolated from thermophilic microorganisms, or may be designed by the skilled person and artificially synthesized. In one embodiment the polynucleotides may be isolated from thermophilic filamentous fungi. Examples of thermophilic filamentous fungi from which polynucleotides encoding thermostable enzymes may be isolated are: *Acremonium, Aureobasidium, Cryptococcus, Filibasidium, Fusarium, Humicola, Magnaporthe, Mucor, Myceliophthora, Neurospora, Paecilomyces, Penicillium, Schizophyllum, Talaromyces, Thermoascus, Thielavia,* and *Tolypocladium*.

In a special aspect of the invention the at least four different polynucleotides are at least the polynucleotides encoding a cellobiohydrolase I and/or a cellobiohydrolase II, an endoglucanase and a β-glucosidase.

Preferably, the polynucleotide encoding the cellobiohydrolase I has at least 70%, more preferably at least 75%, more preferably at least 80%, more preferably at least 85%, more preferably at least 87%, for example at least 90%, for example at least 93%, for example at least 95%, for example at least 96%, for example at least 97%, for example at least 98%, for example at least 99% or 100% identity with SEQ ID No. 2 (polynucleotide encoding cellobiohydrolase I from *Talaromyces emersonii* CBS 39364).

Preferably, the polynucleotide encoding the cellobiohydrolase II has at least at least 70%, more preferably at least 75%, more preferably at least 80%, more preferably at least 85%, more preferably at least 87%, for example at least 90%, for example at least 93%, for example at least 95%, for example at least 96%, for example at least 97%, for example at least 98%, for example at least 99% or 100% % identity with SEQ ID No. 8 (polynucleotide encoding cellobiohydrolase II from *Talaromyces emersonii* CBS 39364).

Preferably, the polynucleotide encoding the endoglucanase has at least at least 70%, more preferably at least 75%, more preferably at least 80%, more preferably at least 85%, more preferably at least 87%, for example at least 90%, for example at least 93%, for example at least 95%, for example at least 96%, for example at least 97%, for example at least 98%, for example at least 99% or 100% % identity with SEQ ID No. 4 (polynucleotide encoding endoglucanase from *Talaromyces emersonii* CBS 39364).

Preferably, the polynucleotide encoding the β-glucosidase has at least at least 70%, more preferably at least 75%, more preferably at least 80%, more preferably at least 85%, more preferably at least 87%, for example at least 90%, for example at least 93%, for example at least 95%, for example at least 96%, for example at least 97%, for example at least 98%, for example at least 99% or 100% % identity with SEQ. ID No. 6 (polynucleotide encoding β-glucosidase from *Talaromyces emersonii*).

In a special embodiment of the invention, the polynucleotide encoding cellobiohydrolase I having at least 70% identity with SEQ ID No. 2 (polynucleotide encoding cellobiohydrolase I from *Talaromyces emersonii* CBS 39364), the polynucleotide having at least 70% identity with SEQ ID No. 8 (polynucleotide encoding cellobiohydrolase II from *Talaromyces emersonii* CBS 39364), the polynucleotide encoding having at least 70% identity with SEQ ID No. 4 (the polynucleotide encoding endoglucanase from *Talaromyces emersonii* CBS 39364) and the polynucleotide having at least 70% identity with SEQ ID No. 6 (the polynucleotide encoding β-glucosidase from *Talaromyces emersonii*) are present in the host cell, preferably an *Aspergillus* host cell.

*Aspergillus* is a very good host cell for the polynucleotides of *Talaromyces emersonii*: cellobiohydrolase I of SEQ ID No. 2, cellobiohydrolase II of SEQ ID No. 8, endogluconase of SEQ ID No. 4 and β-glucosidase of SEQ ID No. 6) and those polynucleotides having at least 70% identity therewith. Surprisingly, it has been found that cellobiohydrolase I of SEQ ID No. 2, cellobiohydrolase II of SEQ ID No. 8, endogluconase of SEQ ID No. 4 and β-glucosidase of SEQ ID No. 6) are expressed in and secreted by *Aspergillus* without any adaptation of these sequences to the preferred codon usage and signal sequences of *Aspergillus*.

Preferably, the polynucleotides encoding the at least four different enzymes chosen from the group of cellulases, hemicellulases and pectinases are original or codon optimized polynucleotides originating from a *Talaromyces* strain, more preferably from a *Talaromyces emersonii* strain, more preferably from the *Talaromyces emersonii* strain deposited at CENTRAAL BUREAU VOOR SCHIMMELCULTURES, Uppsalalaan 8, P.O. Box 85167, NL-3508 AD Utrecht, The Netherlands on 1 Jul. 2009 having the Accession Number CBS 39364, or a functionally equivalent mutant thereof. This latter strain is indicated herein as *Talaromyces emersonii* CBS 39364.

Amino acid or nucleotide sequences are said to be homologous when exhibiting a certain level of similarity. Whether two homologous sequences are closely related or more distantly related is indicated by "percent identity" or "% identity", which is high or low respectively.

For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss-.bioinformatics.nl). For protein sequences, EBLOSUM62 is used for the substitution matrix. For nucleotide sequences, EDNAFULL is used. Other matrices can be specified. For purpose of the invention, the parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The protein sequences mentioned herein can further be used as a "query sequence" to perform a search against sequence databases, for example to identify other family members or related sequences. Such searches can be performed using the BLAST programs. Software for performing BLAST analyses is publicly available through the National Center for Biotechnology Information (www.ncbi.nlm.nih.gov) BLASTP is used for amino acid sequences and BLASTN for nucleotide sequences. In the BLAST program, the default settings may be used:

Cost to open gap: default=5 for nucleotides/11 for proteins

Cost to extend gap: default=2 for nucleotides/1 for proteins

Penalty for nucleotide mismatch: default=−3

Reward for nucleotide match: default=1

Expect value: default=10

Wordsize: default=11 for nucleotides/28 for megablast/3 for proteins

The nucleic acid sequences as mentioned herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to the nucleic acid molecules of the invention.

Homologous polynucleotide sequences can be isolated, for example, by performing PCR using two degenerate oligonucleotide primer pools designed on the basis of nucleotide sequences as mentioned herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new nucleic acid sequence, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines using a standard terminal transferase reaction, the hybrid can be digested with RNase H, and second strand synthesis can than be primed (e.g., with a poly-C primer). Thus, cDNA sequences upstream of the amplified fragment can easily be isolated. For a review of useful cloning strategies, see e.g., Sambrook et al., infra.

For example, with the term at least 70% identity with a sequence listing of an amino acid sequence is meant that the percentage obtained from following the method described above, the percentage obtained is 70% or higher.

Process for the Preparation of the Host Cell

In another aspect, the invention relates to a process for the preparation of a host cell according to the invention comprising the steps of:

(a) Providing one or more expression cassettes comprising at least four different heterologous polynucleotides chosen from the group of polynucleotides encoding cellulases, hemicellulases and pectinases and the control sequences required for expression of these polynucleotides (b) Providing a selectable marker (c) Transforming cells with the one or more expression cassettes and the selectable marker from step (b)

(d) Selecting the thus formed host cells that produce the at least four different cellulases, hemicellulases and/or pectinases encoded by the at least four different heterologous polynucleotides.

The term "nucleic acid construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "operably linked" is defined herein as a configuration in which a control sequence is appropriately placed at a position relative to the coding sequence of the DNA sequence such that the control sequence directs the production of a polypeptide.

The term "control sequences" is defined herein to include all components, which are necessary or advantageous for the expression of mRNA and/or a polypeptide, either in vitro or in a host cell. Each control sequence may be native or foreign to the nucleic acid sequence encoding the polypeptide. Such control sequences include, but are not limited to, a leader. Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals. Control sequences may be optimized to their specific purpose. Preferred optimized control sequences used in the present invention are those described in WO2006/077258, which is herein incorporated by reference.

The control sequences may be provided with linkers for the purpose of introducing specific restriction sites facilitating ligation of the control sequences with the coding region of the nucleic acid sequence encoding a polypeptide.

The control sequence may be an appropriate promoter sequence (promoter).

The control sequence may also be a suitable transcription terminator (terminator) sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention.

Preferred terminator sequences for filamentous fungal cells are obtained from the polynucleotides encoding *A. oryzae* TAKA amylase, *A. niger* glucoamylase (glaA), *A. nidulans* anthranilate synthase, *A. niger* alpha-glucosidase, trpC and *Fusarium oxysporum* trypsin-like protease.

The control sequence may also be a suitable leader sequence (leaders), a non-translated region of an mRNA which is important for translation by the filamentous fungal cell. The leader sequence is operably linked to the 5'-terminus of the nucleic acid sequence encoding the polypeptide. Any leader sequence, which is functional in the cell, may be used in the present invention.

Preferred leaders for filamentous fungal cells are obtained from the polynucleotides encoding *A. oryzae* TAKA amylase and *A. nidulans* triose phosphate isomerase and *A. niger* glaA and phytase.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3'-terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the polynucleotides encoding *A. oryzae* TAKA amylase, *A. niger* glucoamylase, *A. nidulans* anthranilate synthase. *Fusarium oxysporum* trypsin-like protease and *A. niger* alpha-glucosidase.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter.

Examples of inducible promoters that can be used are a starch-, copper-, oleic acid-inducible promoters. The promoter may be selected from the group, which includes but is not limited to promoters obtained from the polynucleotides encoding *A. oryzae* TAKA amylase, *Rhizomucor miehei* aspartic proteinase, *A. niger* neutral alpha-amylase. *A. niger* acid stable alpha-amylase, *A. niger* or *A. awamori* glucoamylase (glaA), *R. miehei* lipase, *A. oryzae* alkaline protease, *A. oryzae* triose phosphate isomerase. *A. nidulans* acetamidase, the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Preferably, the expression of the at least four polynucleotides encoding cellulase, hemicellulase and/or pectinase is driven by a promoter that is active in glucose containing medium, for example a glucoamylase promoter, preferably the glaA promoter as this makes that the presence of a cellulase inducer is not required.

Therefore, the invention also relates to a host cell capable of producing cellulase in the absence of cellulase inducer in a glucose medium.

Other preferred promoters are the promoters described in WO2006/092396 and WO2005/100573, which are herein incorporated by reference.

In order to facilitate expression and/or translation, the polynucleotide or the nucleic acid construct according to the invention may be comprised in an expression vector such that the polynucleotide(s) encoding the enzyme(s) of interest is operably linked to the appropriate control sequences for expression and/or translation in vitro, or in prokaryotic or eukaryotic host cells.

The expression vector may be any vector (e.g., a plasmid or virus), which can be conveniently subjected to recombinant DNA procedures and can bring about the expression of the nucleic acid sequence encoding the polypeptide(s) of interest. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell.

Preferably, the homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1).

More than one copy of a nucleic acid sequence may be inserted into the cell to increase production of the product encoded by said sequence. This can be done, preferably by integrating into its genome copies of the DNA sequence, more preferably by targeting the integration of the DNA sequence at one of the highly expressed locus defined in the former paragraph. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used.

The vector system may be a single vector or plasmid or two or more vectors or plasmids, which together contain the total DNA to be introduced into the genome of the host cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. The selectable marker may be introduced into the cell on the expression vector as the expression cassette or may be introduced on a separate expression vector.

A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* and *Penicillium* cell are the amdS (see for example EP 635574 B1, EP0758020A2, EP1799821A2, WO 97106261A2) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selectable marker gene is the *A. nidulans* amdS coding sequence fused to the *A. nidulans* gpdA promoter (see EP 635574 B1). Other preferred AmdS markers are those described in WO2006/040358. AmdS genes from other filamentous fungi may also be used (WO 97/06261).

The procedures used to ligate the elements described above to construct the recombinant expression vectors of the present invention are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley InterScience, NY, 1995).

Furthermore, standard molecular cloning techniques such as DNA isolation, gel electrophoresis, enzymatic restriction modifications of nucleic acids. Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

Using the desired polynucleotide sequence as a hybridization probe, nucleic acid molecules used in the invention can be isolated using standard hybridization and cloning techniques (e. g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridizable to a nucleotide sequence according to the invention can be prepared by standard synthetic techniques, e.g., using an automated DNA synthesizer.

Preferably, the host cell, for example *Aspergillus* is engineered to improve the expression of the polynucleotides of interest.

Preferably, the efficiency of targeted integration into the genome of the host cell, i.e. integration in a predetermined target locus, is increased by augmented homologous recombination abilities of the host cell. Such phenotype of the cell preferably involves a deficient hdfA or hdfB as described in WO2005/095624A2. WO2005/095624A2 discloses a preferred method to obtain a filamentous fungal cell comprising increased efficiency of targeted integration.

Optionally, the host cell comprises an elevated unfolded protein response (UPR) compared to the wild type cell to enhance production abilities of a polypeptide of interest. UPR may be increased by techniques described in US2004/0186070A1 and/or US200110034045A1 and/or WO01/72783A2 and/or WO2005/123763A1. More specifically, the protein level of HAC1 and/or IRE1 and/or PTC2 has been modulated, and/or the SEC61 protein has been engineered in order to obtain a host cell having an elevated UPR.

Alternatively, or in combination with an elevated UPR, the host cell is genetically modified to obtain a phenotype displaying lower protease expression and/or protease secretion compared to the wild-type cell in order to enhance production abilities of a polypeptide of interest. Such phenotype may be obtained by deletion and/or modification and/or inactivation of a transcriptional regulator of expression of proteases. Such a transcriptional regulator is e.g. prtT. Lowering expression of proteases by modulation of prtT may be performed by techniques described in US2004/0191864A1.

Alternatively, or in combination with an elevated UPR and/or a phenotype displaying lower protease expression and/or protease secretion, the host cell displays an oxalate deficient phenotype in order to enhance the yield of production of a polypeptide of interest. An oxalate deficient phenotype may be obtained by techniques described in WO2004/070022A2.

Alternatively, or in combination with an elevated UPR and/or a phenotype displaying lower protease expression and/or protease secretion and/or oxalate deficiency, the host cell displays a combination of phenotypic differences compared to the wild cell to enhance the yield of production of the polypeptide of interest. These differences may include, but are not limited to, lowered expression of glucoamylase and/or neutral alpha-amylase A and/or neutral alpha-amylase B, protease, and oxalic acid hydrolase. Said phenotypic differences displayed by the host cell may be obtained by genetic modification according to the techniques described in US2004/0191864A1.

Alternatively, or in combination with an elevated UPR and/or a phenotype displaying lower protease expression and/or protease secretion and/or oxalate deficiency and a combination of phenotypic differences compared to the wild cell to enhance the yield of production of the polypeptide of interest, the host cell displays a deficiency in toxin genes, disabling the ability of the filamentous fungal host cell to express toxins. Such toxins include, but are not limited to, ochratoxins, fumonisins, cyclapiazonic acid, 3-nitropropionic acid, emodin, malformin, aflatoxins and secalonic acids. Such deficiency is preferably such as described in WO2000/039322A1.

The person skilled in the art knows how to transform cells with the one or more expression cassettes and the selectable marker. For example, the skilled person may use one or more expression vectors, wherein the one or more cloning vectors comprise the expression cassettes and the selectable marker.

Transformation of the cells may be conducted by any suitable known methods, including e.g. electroporation methods, particle bombardment or microprojectile bombardment, protoplast methods and *Agrobacterium* mediated transformation (AMT). Preferably the protoplast method is used. Procedures for transformation are described by J. R. S. Fincham, Transformation in fungi. 1989, microbiological reviews. 53, 148-170.

Transformation of the host cell by introduction of a polynucleotide an expression vector or a nucleic acid construct into the cell is preferably performed by techniques well known in the art (see Sambrook & Russell; Ausubel, supra). Transformation may involve a process consisting of protoplast formation, transformation of the protoplasts, and regeneration of the cell wall in a manner known per se. Suitable procedures for transformation of *Aspergillus* cells are described in EP 238 023A2 and Yelton et of, 1984, Proceedings of the National Academy of Sciences USA 81:1470-1474. Suitable procedures for transformation of *Aspergillus* and other filamentous fungal host cells using *Agrobacterium tumefaciens* are described in e.g. De Groot at al., *Agrobacterium tumefaciens-mediated transformation of filamentous fungi*. Nat Biotechnol. 1998, 16:839-842. Erratum in: Nat Biotechnol 1998 16:1074. A suitable method of transforming *Fusarium* species is described by Malardier et al., 1989. Gene 78:147156 or in WO 96/00787A2. Other methods can be applied such as a method using biolistic transformation as described in: Christiansen at al., *Biolistic transformation of the obligate plant pathogenic fungus, Erysiphe graminis* f.sp. *hordei*. 1995, Curr Genet. 29:100-102. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983. Journal of Bacteriology 153: 163; and Hinnen et al., 1978. Proceedings of the National Academy of Sciences USA 75: 1920.

In order to enhance the amount of copies of the polynucleotide of interest in the host cell, multiple transformations of the host cell may be required. In this way, the ratios of the different enzymes produced by the host cell may be influenced. Also, an expression vector may comprise multiple expression cassettes to increase the amount of copies of the polynucleotide(s) be transformed.

Another way could be to choose different control sequences for the different polynucleotides, which—depending on the choice—may cause a higher or a lower production of the desired enzyme(s).

An advantage of the host cell of the invention is that the host cell of the invention can be used for the preparation of an enzyme composition having a consistent composition.

The cells transformed with the selectable marker can be selected based on the presence of the selectable marker. In case of transformation of (*Aspergillus*) cells, usually when the cell is transformed with all nucleic acid material at the same time, when the selectable marker is present also the polynucleotide(s) encoding the desired enzyme(s) are present.

However, in order to ensure that the desired enzymes are produced by the host cell, the host cell can be selected based on the presence of the enzymes in the fermentation broth. The presence of the desired enzyme activity (WSU) can be detected in the fermentation broth as described in the experimental section below. Alternatively, the presence of the desired enzymes can be determined using SDS-PAGE analysis as described in the experimental section below.

The Enzyme Composition

In another aspect, the invention relates to the enzyme composition comprising at least four different cellulases, hemicellulases and/or pectinases produced by the host cell according to the invention.

The enzyme composition may be the unpurified fermentation broth, wherein the host cell has produced and secreted the at least four different cellulases, hemicellulases and/or pectinases, which fermentation broth contains the host cells or it may be a further purified form of the fermentation broth. Methods for purification of enzymes are known to the person skilled in the art (downstream processing as described below).

In one embodiment, CBHI is provided in an enzyme composition that comprises BG, EG and CBHII. In an embodiment thereof, the amounts of enzymes are chosen so that BG is present at 2-12%, CBHI at 10-65%. CBHII at 10-40% and EG at 12-70%, or in an embodiment thereof BG at 4-12%, EG at 18-50%, CBHII at 10-35% and CBHI at 10-60% of the total protein dose (w/w).

A further aspect of the present invention concerns the option of downstream processing of the cultivation broth.

The batch process applied according to the invention facilitates downstream processing, especially because of the high yield of the valuable compound and the low amount of by-products. Downstream processing may include recovery as well as formulation steps.

After the cultivation process is ended, the valuable product may be recovered from the cultivation broth, using standard technology developed for recovery of the valuable compound of interest. The relevant downstream processing technology to be applied thereby depends on the nature and cellular localization of the valuable compound and on the desired purity level of the product of interest. In a typical recovery process, the biomass is separated from the cultivation fluid using e.g. centrifugation or filtration. The valuable compound then is recovered from the biomass in the case that the valuable product is accumulated inside or is associated with the microbial cells. The term "recovering" includes isolating, extracting, harvesting, separating or purifying the compound from culture media. Isolating the compound can be performed according to any conventional isolation or purification methodology known in the art including, but not limited to, alteration of pH, solvent extraction, dialysis, cell filtration and ultrafiltration, concentration, lyophilisation and the like.

In yet another aspect, the invention relates to a process for the production of a enzyme composition according to the invention comprising at least four different cellulases, hemicellulases and/or pectinases comprising the steps of:

(a) providing the host cell of the invention
(b) allowing production and secretion of the at least four different cellulases, hemicellulases and/or pectinases by the host cell and
(c) optional recovering of the thus obtained enzyme composition.

The invention also relates to the enzyme composition obtainable by this process.

For example, a host cell of the invention may be cultured in a suitable medium and under conditions allowing the cellulase mixture to be expressed and/or isolated.

The culture takes place in a suitable nutrient medium comprising carbon and nitrogen sources and inorganic salts, using procedures known in the art (see, e. g., Bennett, J. W. and LaSure, L., eds., More Gene Manipulations in Fungi, Academic Press, CA, 1991). Suitable media are available from commercial suppliers or may be prepared using published compositions e. g., in catalogues of the American Type Culture Collection).

The medium, also mentioned herein as cultivation medium, is not critical to the invention. Nutrients may be added to the process according to the needs of the host cell in question, provided that the nutrients are supplied in excess. The cultivation medium conveniently contains a carbon source, a nitrogen source as well as additional compounds required for growth of the microorganism and/or the formation of the product. For instance, additional compounds may be present for inducing the production of the product. Examples of suitable carbon sources known in the art include glucose, maltose, maltodextrins, sucrose, hydrolysed starch, starch, molasses and oils. Examples of nitrogen sources known in the art include soy bean meal, corn steep liquor, yeast extract, ammonia, ammonium salts and nitrate salts. Examples of additional compounds include phosphate, sulphate, trace elements and vitamins. The total amount of carbon and nitrogen source to be added may vary depending on e.g. the needs of the host cell and/or the time allowed for expression and secretion of the enzymes. The ratio between carbon and nitrogen source may vary considerably, whereby one determinant for an optimal ratio between carbon and nitrogen source may be the elemental composition of the product to be formed. Additional compounds required for growth of the host cell and/or for product formation, like phosphate, sulphate or trace elements, may be added in amounts that may vary between different classes of the host cell. i.e. between fungi, yeasts and bacteria. In addition, the amount of additional compound to be added may be determined by the type of product formed.

With 'recovering of the thus obtained enzyme composition' is meant that the enzyme composition may be separated from the host cell and other components that are not the desired enzymes (see downstream processing as described above).

Preferably, the host cell is allowed to produce and secrete the at least four different cellulases, hemicellulases and/or pectinases in a glucose containing medium, which glucose containing medium preferably does not contain a cellulase inducer for reasons as described herein.

Of course, the enzyme composition of the present invention may also comprise further components, for example proteins, such as enzymes; or other components.

In case of proteins, these proteins may have been produced and secreted by the host cell, but they may have been separately added to the enzyme composition.

For example, the enzyme composition may comprise an auxiliary enzyme activity. Such additional activities may be derived from classical sources and/or produced by a genetically modified organism.

Therefore, in addition, one or more (for example two, three, four or all) enzymes chosen from the group of amylases, proteases, preferably from the group of proteases that do not degrade the cellulases, hemicellulases and/or pectinases present in the enzyme composition; lipases, ligninases, hexosyltransferases, glucuronidases, expansins, cellulose induced proteins, cellulose integrating proteins and other proteins may be present in the enzyme composition of the invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like, in plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

The enzyme composition may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition of the invention may comprise the polypeptide product of a cellulose integrating protein, scaffoldin or a scaffoldin-like protein, for example CipA or CipC from *Clostridium thermocellum* or *Clostridium cellulolyticum* respectively.

Scaffoldins and cellulose integrating proteins are multifunctional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate, A scaffoldin or cellulose integrating protein for the purposes of this invention may comprise one or both of such domains.

A composition of the invention may comprise a cellulose induced protein or modulating protein, for example as encoded by cip1 or cip2 gene or similar genes from *Trichoderma reesei/Hypocrea jacorina* (see Foreman et al., J. Biol. Chem. 278(34), 31988-31997, 2003). The polypeptide products of these genes are bimodular proteins, which contain a cellulose binding module and a domain which function or activity can not be related to known glycosyl hydrolase families. Yet, the presence of a cellulose binding module and the coregulation of the expression of these genes with cellulases components indicates previously unrecognised activities with potential role in biomass degradation.

A composition of the invention may be composed of a member of each of the classes of the polypeptides mentioned above, several members of one polypeptide class, or any combination of these polypeptide classes.

A composition of the invention may be composed of polypeptides, for example enzymes, from (1) commercial suppliers; (2) cloned genes expressing polypeptides, for example enzymes; (3) complex broth (such as that resulting from growth of a microbial strain in media, wherein the strains secrete proteins and enzymes into the media; (4) cell lysates of strains grown as in (3); and/or (5) plant material expressing polypeptides, for example enzymes. Different polypeptides, for example enzymes in a composition of the invention may be obtained from different sources.

The activities in the enzyme composition may be thermostable. Herein, this means that the activity has a temperature optimum of about 60° C. or higher, for example about 70° C. or higher, such as about 75° C. or higher, for example about 80° C. or higher such as 85° C. or higher. Activities in the enzyme composition will typically not have the same temperature optima, but preferably will, nevertheless, be thermostable.

In addition, enzyme activities in the enzyme composition may be able to work at low pH. For the purposes of this invention, low pH indicates a pH of about 5.5 or lower, about 5 or lower, about 4.5 or lower, about 4.0 or lower or about 3.8 or lower or about 3.5 or lower.

Activities in the enzyme composition may be defined by a combination of any of the above temperature optima and pH values.

Industrial Application of the Enzyme Composition

In principle, an enzyme composition of the invention may be used in any process which requires the treatment of a material which comprises non-starch polysaccharide. Thus, a polypeptide or enzyme composition of the invention may be used in the treatment of non-starch polysaccharide material. Herein, non-starch polysaccharide material is a material which comprises or consists essential of one or, more typically, more than one non-starch polysaccharide.

Typically, plants and fungi and material derived therefrom comprise significant quantities of non-starch polysaccharide material. Accordingly, a polypeptide of the invention may be used in the treatment of a plant or fungal material or a material derived therefrom.

An important component of plant non-starch polysaccharide material is lignocellulose (also referred to herein as lignocellulolytic biomass). Lignocellulose is plant material that is composed of cellulose and hemicellulose and lignin. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a non-starch polysaccharide in which the treatment comprises the degradation and/or modification of cellulose and/or hemicellulose.

Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants and fungi contain non-starch polysaccharide as do virtually all plant- and fungal-derived polysaccharide materials. Accordingly, in a method of the invention for the treatment of a non-starch polysaccharide, said non-starch polysaccharide may be provided in the form of a plant or a plant derived material or a material comprising a plant or plant derived material, for example a plant pulp, a plant extract, a foodstuff or ingredient therefore, a fabric, a textile or an item of clothing.

The enzyme compositions of the invention can extremely effectively hydrolyze lignocellulolytic material, for example corn stover or wheat straw, into monomeric sugars (the hydrolysis of lignocellulosic material is also referred to herein as saccharification of lignocellulosic material) which can then be further converted into a useful product, such as ethanol.

Therefore, in another aspect, the invention relates to a process for the saccharification of lignocellulosic material comprising the steps of
optional pretreatment of lignocellulosic material and
contacting the lignocellulosic material with a enzyme composition according to the invention to produce one or more sugars.

The enzyme compositions of the invention can be used to carry out highly effective hydrolysis of a lignocellulosic substrate. This is highly significant in the context of commercially viable fuel ethanol production from lignocellulosic biomass since lower amounts of enzyme will be required (as compared with currently available products).

In addition, currently available enzymes having cellulase activity, typically derived from *Trichoderma*, function at mesophilic temperatures, such as from 45° C. to 50° C. and at pH 5.0. This, however, may lead to bacterial infection reducing product yield, so it is desirable to carry out saccharification at a temperature of 65° C. or higher. In addition, the use of mesophilic temperatures increases the viscosity of the biomass being used such that the dry matter content used is limited. Also, when acid pretreated biomass is used as a substrate, the pH must be raised no that the enzyme can saccharify the sugars in the biomass. In the context of a commercially viable fuel ethanol industry, this implies a requirement for, for example, sodium hydroxide or calcium sulphate and the production of huge quantities of the corresponding salts, for example gypsum in the case of sodium hydroxide. Accordingly, it is desirable to carry out saccharification using an enzyme which can operate at a pH of pH 4.0 or lower.

Moreover, this hydrolysis may be carried out at a high temperature especially, if the polynucleotides encoding the at least four different enzymes chosen from the group of polynucleotides encoding cellulases, hemicellulases and pectinases are polynucleotides originating from a *Talaromyces* strain, for example from a *Talaromyces emersonii* strain.

Hydrolysis of a lignocellulosic substrate at a higher temperature, for example at a temperature of 65° C. or higher, is favorable as it (i) reduces the risk of bacterial infection and (ii) results in a less viscous biomass pulp. The effect of the latter is significant since it enables the better blending of enzymes, resulting in a higher operational dry matter in the plant and allows a consequent higher ethanol concentration to be achieved. Thus, less energy need be used improving sustainability and a smaller fermentation process will be required requiring lower investment.

A pretreatment of the lignocellulosic material usually occurs at high temperature; therefore if the polynucleotides encoding the at least four different enzymes are chosen from the group of polynucleotides encoding cellulases, hemicellulases or pectinases are polynucleotides originating from a *Talaromyces* strain, for example from a *Talaromyces emersonii* strain, there is no need to completely cool the lignocellulosic material to low temperatures, such as below 40° C. before the enzyme composition is added. Instead, the enzyme composition may for example be added to the lignocellulosic material having a temperature of up to 80° C., for example to lignocellulosic material having a temperature in the range of from 60 to 80° C., for instance at about 65° C.

This shortens the process for the saccharification of lignocellulosic material considerably, as well as provides for a greener route. The reason for this is that addition of enzymes at higher temperatures requires less cooling of the pre-treated lignocellulosic materials, which saves energy, and enzymes can be added earlier to the lignocellulosic material, which saves time.

For example, the hydrolysis of the lignocellulosic material by the enzyme composition of the invention may be performed at a temperature of at least 30° C., for example of at least 37° C., for example of at least 40° C., for example of at least 50° C., for example of at least 56° C., for example of at least 60° C., for example of at least 65'C, for example of at least 70° C.

For example, the hydrolysis of the lignocellulosic material by the enzyme composition of the invention may be performed at a temperature of at most 100° C., for example of at most 90° C., for example of at most 80° C., for example of at most 70° C.

Also, this hydrolysis may be carried out at low pH, for example at a pH of pH 4.0 or lower. This is desirable since biomass is often pretreated with acid. Biomass treated in this way does not have to be pH adjusted if the enzymes subsequently used for saccharification are capable of acting at low pH. This implies a lower requirement of, for example, sodium hydroxide or calcium sulphate and a process in which there is no waste salt. This is significant in a process in which, for example, fuel ethanol is to be produced since huge quantities of material are consumed in such processes. This allows the process according to the invention to be carried out with no or little pH adjustment is required, i.e. there is no or a reduced requirement for the addition of acids or bases. The process may thus be carried out as a zero or low waste process (no or low salt production) and/or as a process in which no or little inorganic chemical input is required.

In addition, it has been shown that the enzyme composition can effectively hydrolyze biomass when high dry matter contents are used. It is highly desirable that enzymes used in the production of, for example, fuel ethanol are able to operate on substrates having high viscosity (i.e. high dry weight composition) since this allows higher amounts of the final product, for example, fuel ethanol, to be achieved.

Significantly, a method of the invention may be carried out using high levels of dry matter (of the lignocellulosic material) in the hydrolysis reaction. Thus, the invention may be carried out with a dry matter content of about 5% or higher, about 8% or higher, about 10% or higher, about 15% or higher, about 20% or higher, about 25% or higher, about 30% or higher, about 35% or higher or about 40% or higher.

Preferably in the method, the lignocellulosic material is orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, sugar cane, corn stover, corn stalks, corn cobs, corn husks, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, softwood, poplar, pine, shrubs, grasses, wheat, sugar cane bagasse, corn, corn hobs, corn kernel, fiber from kernels, products and by-products from wet or dry milling of grains, municipal solid waste, waste paper, yard waste, herbaceous material, agricultural residues, forestry residues, waste paper, pulp, paper mill residues, branches, bushes, canes, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

The composition is reacted with substrate under any appropriate conditions. For example, enzymes can be incubated at about 25° C., about 30° C., about 35° C., about 37° C., about 40° C., about 45° C. about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimolar (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 9.

Typically, the reaction may be carried out under low pH conditions as defined above. Thus, a method of the invention may be carried out such that no pH adjustment (i.e. to a more neutral pH is required). That is to say, an acid pretreated feedstock may be used as is with no requirement to addition of, for example, sodium hydroxide, prior to addition of an enzyme composition of the invention.

The feedstock may be washed prior to liquefaction/hydrolysis. Such washing may be with, for example, water.

Incubation of a composition under these conditions results in release or liberation of substantial amounts of the sugar from the lignocellulosic material. By substantial amount is intended at least about 20%, at least about 30%, at least about 40%, at least about 50%, at least about 60%, at least about 70%, at least about 80%, at least about 90%, at least about 95% or more of available sugar.

A liquefaction/hydrolysis or presaccharification step involving incubation with an enzyme or enzyme mixture can be utilized. This step can be performed at many different temperatures but it is preferred that the presaccharification occur at the temperature best suited to the enzyme mix being tested, or the predicted enzyme optimum of the enzymes to be tested. The temperature of the pretreatment may range from about 10° C. to about 100° C., about 30° C. to about 80° C., about 40° C. to about 70° C., about 50° C. to about 70° C., preferably about 60° C. to about 70° C., more preferably about 65° C. In the absence of data on the temperature optimum, it is preferable to perform the pretreatment reactions at 37° C. first, then at a higher temperature such as 65° C. The pH of the presaccharification mixture may range from about 2.0 to about 10.0, but is preferably about 3.0 to about 5.0. Again, it may not be necessary to adjust the pH prior to saccharification since the enzyme composition is typically suitable for use at low pH as defined herein.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The liquification/hydrolysis may occur from several minutes to several hours, such as from about 6 hours to about 168 hours, preferably about 12 hours to about 96 hours, more preferably about 24 hours to about 72 hours, even more preferably from about 24 hours to about 48 hours.

Depending on the application, e.g. when the enzymes or enzyme composition are used in a process where liquefaction/hydrolysis is combined with fermentation, the process may be carried out as separate hydrolysis and fermentation (SHF) and simultaneous hydrolysis and fermentation (SSF). In SSF a presaccharifation may be appropriate. SHF and SSF will be described in more detail below.

The invention further relates to a method for the conversion of lignocellulosic material into useful product comprising the following steps: a) pretreatment of one or more lignocellulosic material to produce pretreated lignocellulosic material; b) enzymatic treatment of the pretreated lignocellulosic material to produce one or more sugar; c) converting the sugar into one or more useful product and d) separating the one or more useful products, wherein in step a), b) or c) an enzyme composition of the invention is used or added.

Therefore, the invention also relates to a process for the preparation of a fermentation product, including amino acids, vitamins, pharmaceuticals, animal feed supplements, specialty chemicals, chemical feedstocks, plastics, solvents, fuels, or other organic polymers, lactic acid, ethanol, fuel ethanol or chemicals, plastics, dicarboxylic acids, such as for example succinic acid, itaconic acid, adipic acid; (bio) fuels, including ethanol, methanol, butanol, synthetic liquid fuels and biogoas, wherein the one or more sugars that is or are produced according to the process of the invention, is fermented with a fermenting microorganism, preferably yeast to produce the fermentation product.

With 'fermenting microorganism' is meant a microorganism having the ability to convert the one or more sugars into the fermentation product.

Such a process may be carried out without any requirement to adjust the pH during the process. That is to say, the process is one which may be carried out without the addition of any acid(s) or base(s). However, this excludes a pretreatment step, where acid may be added. The point is that the enzyme composition of the invention is capable of acting at low pH and, therefore, there is no need to adjust the pH of acid of an acid pretreated feedstock in order that saccharification may take place. Accordingly, a method of the invention may be a zero waste method using only organic products with no requirement for inorganic chemical input.

Preferably, in the method according to the invention, the useful product is one or more of ethanol, butanol, lactic acid, a plastic, an organic acid, a solvent, an animal feed supplement, a pharmaceutical, a vitamin, an amino acid, an enzyme or a chemical feedstock. The present invention provides relates to a composition which comprises cellulolytic and/or hemicellulolytic enzyme activity and which has the ability to modify, for example degrade, a non-starch carbohydrate material. Anon-stanch carbohydrate material is a material which comprises, consists of or substantially consists of one or more non-starch carbohydrates. Carbohydrate in this context includes all saccharides, for example polysaccharides, oligosaccharides, disaccharides or monosaccharides.

A composition as described herein typically modifies a non-starch carbohydrate material by chemically modification of such material. Chemical modification of the carbohydrate material may result in the degradation of such material, for example by hydrolysis, oxidation or other chemical modification such as by the action of a lyase.

A non-starch carbohydrate suitable for modification by a composition as described herein is lignocellulose. The major polysaccharides comprising different lignocellulosic residues, which may be considered as a potential renewable feedstock, are cellulose (glucans), hemicelluloses (xylans, heteroxylans and xyloglucans), in addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

A method for the preparation of a fermentation product may optionally comprise recovery of the fermentation product.

Such a process may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h. A method for the preparation of a fermentation product may optionally comprise recovery of the fermentation product.

In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 g/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and
b. fermenting the resulting material,
thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The invention will now be elucidated by way of the following examples, without however being limited thereto.

Example 1

Expression of Multiple *Talaromyces Emersonii* Cellulases in *Aspergillus Niger*

This example describes the cloning and expression of *T. emersonii* CBS 39364 cellobiohydrolase-I (CBHI), *T. emersonii* CBS 39364 cellobiohydrolase-II (CBHII). *T. emersonii* β-glucanase CEA CBS 39364 (EG), and *T. emersonii* β-glucosidase (BG) as presented in the GenBank database with accession number AAL69548 in *A. niger* WT-1. In addition, cellulase activity of transformants is compared with cellulase activity of an empty strain after growing the strains in shake flasks.

Cloning of *T. emersonii* Coding Regions in Expression Vectors

The polynucleotides (DNA-sequences) encoding *T. emersonii* cellobiohydrolase-I (CBHI), *T. emersonii* beta-glucanase CEA (EG), and *T. emersonii* β-glucosidase (BG) were synthesised by DNA2.0 (Menlo Park, USA) and cloned as EcoRI/SnaBI fragment into the pGBTOP-8 vector (EP 0635574A1), comprising the glucoamylase (glaA) promoter and terminator sequence, resulting in vector pGBTOP-EBA205, pGBTOPEBA8 and pGBTOPEBA4, respectively. For cloning purposes, 198 nucleotides of the 3' part of the glucoamylase promoter was also synthesised with the coding sequences. The amino acid sequences of the *T. emersonii* cellobiohydrolase-I (GBHI), *T. emersonii* beta-glucanase CEA (EG), and *T. emersonii* β-glucosidase (BG) are represented by SEQ ID NO: 1, 3, and 5, respectively. The DNA sequences are represented by SEQ ID NO: 2, 4 and 6, respectively. FIG. 1 represents a map of a pGBTOPEBA205 containing the DNA-sequence encoding the *T. emersonii* CBHI under control of the glaA promoter within vector pGBTOP12. pGBTOPEBA205 is representative for pGB-TOPEBA8, which comprises the DNA-sequence encoding the *T. emersonii* EG, and pGBTOPEBA4, which comprises DNA-sequence encoding the *T. emersonii* BG.

Figure 2:
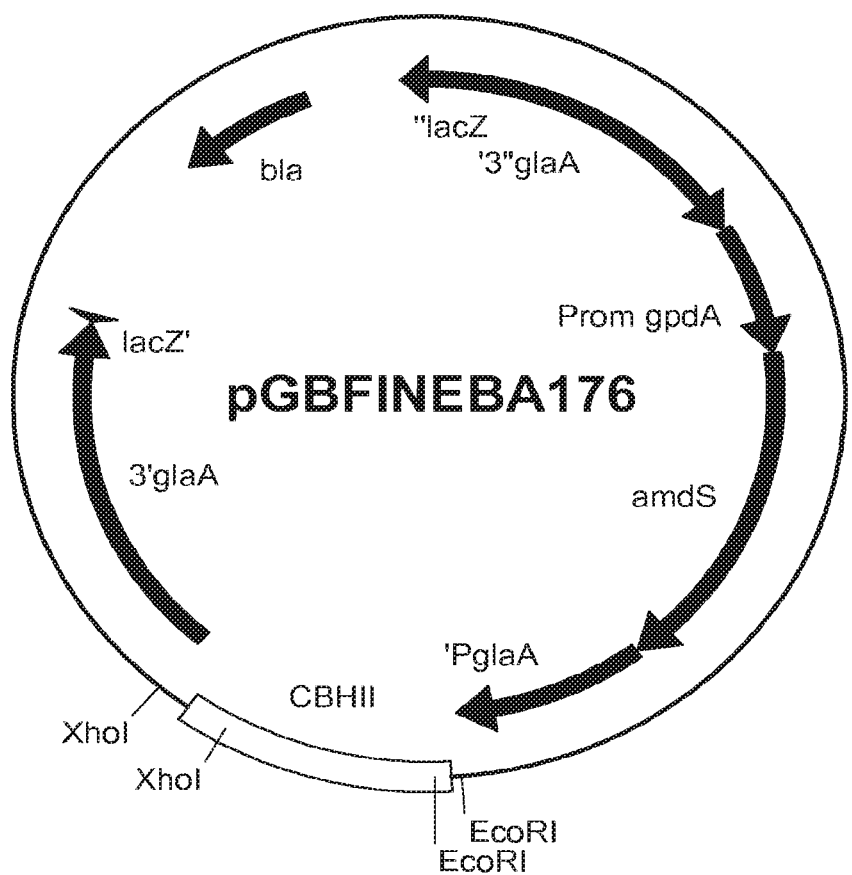
FIG. 2: Map of pGBFINEBA176 for expression of *T. emersonii* cellobiohydrolase II (CBHII) in *T. emersonii*. pGBFINEBA176 is a pGBFIN11-based plasmid. Depicted is EBA176 expressed from the glucoamylase promoter (PglaA). In addition, the selectable marker (amdS), expressed from the *Aspergillus nidulans* glyceraldehyde-3-phosphate dehydrogenease promoter (Pgpd) and the glucoamylase flanks (3'glaA and 3"glaA) of the expression cassette are depicted.

The polynucleotide encoding *T. emersonii* cellobiohydrolase-II (CBHII), was obtained from a *T. emersonii* cDNA library as described in patent WO2001/070998 A1. FIG. 2 represents a map of pGBFINEBA176 containing the DNA-sequence encoding the *T. emersonii* CBHII under control of the glaA promoter within vector pGBFIN11 (WO 9932617 (A2)). The pGBFIN11 vector also contains the selection marker, AmdS (EP0758020 (A2)), which selects for the ability to use acetamide as sole nitrogen source. The amino acid sequence and nucleotide sequence are represented by SEQ ID NO: 7 and 8, respectively.

Transformation of *Aspergillus niger* with Multiple Cellulases

*Aspergillus niger* WT-1 strain was used for transformations. The *Aspergillus niger* WT-1 strain is derived from the *A. niger* strain deposited at the CBS Institute under the deposit number CBS 513.88 (Pel et al., *Genome sequencing and analysis of the versatile cell factory Aspergillus niger* CBS 513.88. 2007, Nat Biotechnol. 25:189-90). It comprises a deletion of the gene encoding glucoamylase (glaA), which was constructed by using the "MARKER-GENE FREE" approach as described in EP 0635574 (A1). In this patent application it is extensively described how to delete glaA specific DNA sequences in the genome of CBS 513.88. The procedure resulted in a MARKER-GENE FREE ΔglaA recombinant *A. niger* CBS513.88 strain, possessing finally no foreign DNA sequences at all.

In order to introduce the pGBTOPEBA vectors and pGB-FINEBA176 in *Aspergillus niger* WT-1, transformation and subsequent transformant selection was carried out essentially as described in WO 9846772 (A2) and WO 9932617 (A2). In brief, linear DNA of the vector was isolated after digestion with NotI, to remove the *E. coli* sequences from the vector. After transformation of the cells with the linear DNA, transformants were selected on media comprising acetamide as sole nitrogen source and colony purified.

Transformants were cultured in shake flasks in 100 ml of CSM-MES medium as described in EP 635 574 A1 at 34° C. at 170 rpm in an incubator shaker using a 500 ml baffled shake flask. After different time-points of fermentation, supernatant samples were harvested to determine expression by SOS-PAGE analysis, Protein samples were separated under reducing conditions on NuPAGE 4-12% Bis-Tris gel (Invitrogen, Breda, The Netherlands) and stained with Sypro Ruby (Invitrogen, Breda, The Netherlands)) according to manufacturer's instructions.

Figure 3A:
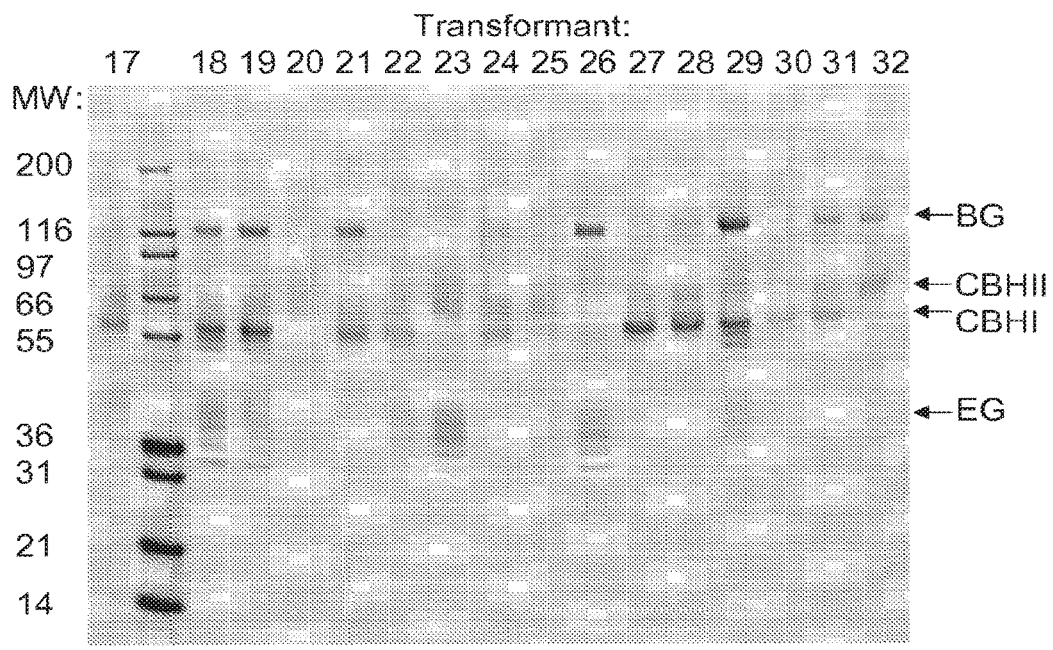
FIGS. 3A-3B: Detection of multiple recombinant *T. emersonii* cellulases in *A. niger*. (3A). SDS-PAGE detection of *T. emersonii* cellulases expressed in *A. niger*. *A. niger* was transformed with a mix of pGBTOPEBA4, pGBTOPEBA8, pGBFINEBA176, and pGBTOPEBA205. Transformants were grown in shake flasks containing maltose containing medium and proteins in supernatants harvested from 96 hours cultures were analysed by SDS-PAGE analysis. (3B). Graph showing WSU activity in transformants. Transformants were grown for 96 hours in maltose containing medium and WSU activity was determined in supernatants of the cultures.

FIG. 3A shows the SOS-PAGE gel of a subset of tested transformants expressing multiple cellulases. The theoretical molecular weights of the proteins encoded by pGBTOP-EBA4, pGBTOPEBA8, pGBFINEBA176 and pGBTOP-EBA205 are shown in Table 1.

TABLE 1

Theoretical molecular weight of the proteins encoded by pGBTOPEBA4, pGBTOPEBA8, pGBFINEBA176 and pGBTOPEBA205

| Construct | Protein encoded by construct | Theoretical molecular weight |
| --- | --- | --- |
| pGBTOPEBA4 | BG | 92 kDa |
| pGBTOPEBA8 | EG | 37 kDa |
| pGBFINEBA176 | GBHII | 48 kDa |
| pGBTOPEBA205 | CBHI | 49 kDa |

As expected, different combinations of overexpressed cellulases were observed. From the SOS-PAGE analysis a host cell capable of expressing and secreting the at least four different cellulases, such as for example transformant 19, can be selected.

To determine whether the transformants were able to degrade pre-treated wheat straw a WSU assay was performed to determine cellulase activity.

Wheat Straw Assay (WSU Assay)

In order to measure cellulase activity a WSU activity assay was performed. WSU activity was measures in supernatants (the liquid part of the broth wherein the cells were cultured) of an empty strain and the transformant:

Preparation of Pre-Treated, Washed Wheat Straw Substrate

Dilute-acid pre-treated wheat straw which was washed with water until the solution with wheat straw was pH 6.5 or higher and the mass was homogenised using an ultra-turrax, lyophilized and grinded prior to analysis. To obtain pre-treated wheat straw a dilute acid pre-treatment as described in Linde. M. et al. Biomass and Bioenergy 32 (2008), 326-332 and equipment as described in Schell, D. J., Applied Biochemistry and Biotechnology (2003), vol. 105-108, pp 69-85, may be used.

With 1 WSU is meant 0.119 mg/ml glucose released from 2.1 w/v % washed pre-treated wheat straw by 200 μl of enzyme mix in 20 hours at 65° C. at pH 4.50.

The glucose release is not a linear function of the quantity of enzyme in the composition. In other words, twice the amount of enzyme does not automatically result in twice the amount of glucose in equal time. Therefore, it is preferred to choose the dilution of the composition to be tested for WSU activity such that a WSU does not exceed 40.

Measurement of Cellulase Activity in WSU/ml

400 μl of supernatants harvested from shake flask experiments were diluted 16-fold. Diluted sample was used to perform two measurements in which 200 μl of diluted sample was analysed. In the first measurement, 200 μl diluted sample was transferred to a vial containing 700 μL water containing 3% (w/v) dry matter of the pretreated washed wheat straw substrate and 100 μl of 250 mM citrate buffer, the final pH was adjusted to pH 4.5. In the second measurement, the blank sample, 200 μl of diluted sample was transferred to a vial that contained 700 μl of water instead of pretreated washed wheat straw substrate, and 100 μl of 250 mM citrate buffer, the final pH was adjusted to pH 4.5. The assay samples were incubated for 20 and/or 60 hr at 65° C. After incubation of the assay samples, 100 μl of internal standard solution (20 g/L maleic acid, 40 g/L EDTA in $D_2O$) was added. The amount of glucose released, was based on the signal at 5.20 ppm, relative to Dimethyl-sila-pentane-sulfonate determined by means of 1D $^1H$ NMR operating at a proton frequency of 500 MHz, using a pulse program with water suppression, at a temperature of 27° C. The WSU number was calculated from the data by subtracting by the amount of glucose that was detected in the blank sample from the amount of glucose that was measured in the sample incubated with wheat straw.

Figure 3B:
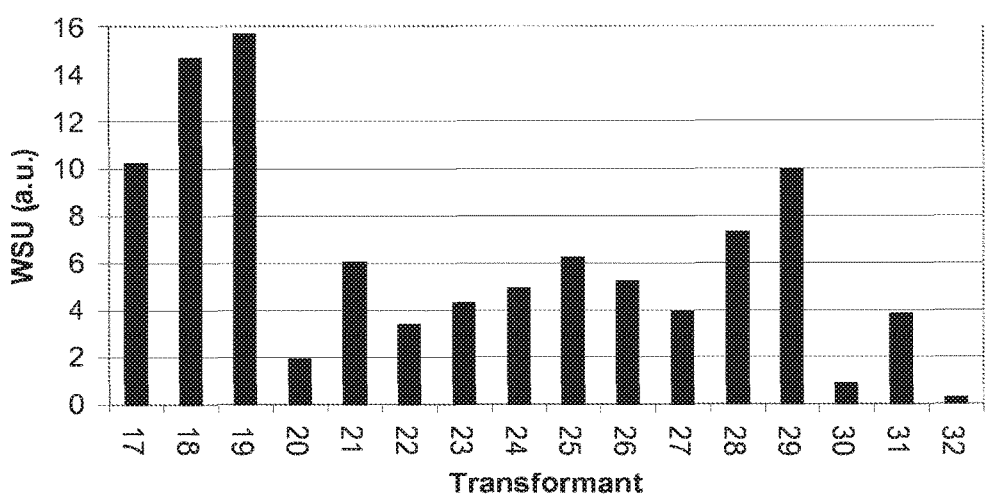

The results of the WSU assay are shown in FIG. 3B. In supernatants of strains expressing a single cellulase or in empty strains, no WSU activity could be measured. In *A. niger* transformants expressing all four cellulases, e.g. transformant 18 and 19, up to 17 WSU/ml was measured.

The experiment indicates that pGBTOPEBA4, pGBTOP-EBA8, pGBFINEBA176 and pGBTOPEBA205 are expressed in *A. niger* and that *A. niger* strains overexpressing multiple *T. emersonii* cellulases in maltose-containing medium are able to degrade pre-treated wheat straw1.

Materials and Methods (Example 2)

Fermentation Medium:

| *Talaromyces* medium 1 | |
| --- | --- |
| Glucose | 20 g/L |
| Yeast extract (Difco) | 20 g/L |
| Clerol FBA3107 (AF) | 4 drops/L |
| pH | 6.0 |
| Sterilize | 20 min at 120° C. |
| *Talaromyces* medium 2 | |
| Salt fraction | 15 g |
| Cellulose | 30 g |
| Bacto peptone | 7.5 g |
| Grain flour | 15 g |
| $KH_2PO_4$ | 10 g |
| $CaCl_2 \cdot 2H_2O$ | 0.5 g |
| Clerol FBA3107 (AF) | 0.4 ml |
| pH | 5 |
| Water | Adjust to one liter |
| Sterilize | 20 min at 120° C. |
| *Talaromyces* medium 3 | |
| Salt fraction | 15 g |
| Glucose | 50 g |
| Bacto peptone | 7.5 g |
| $KH_2PO_4$ | 10 g |
| $CaCl_2 \cdot 2H_2O$ | 0.5 g |
| Clerol FBA3107 (AF) | 0.4 ml |
| pH | 5 |
| Water | Adjust to one liter |
| Sterilize | 20 min at 120° C. |

Spore Batch Preparation

Strains were grown from stocks on *Talaromyces* agar medium in 10 cm diameter Petri dishes for 5-7 days at 40° C. Strain stocks were stored at −80° C. in 10% glycerol.

Shake Flask Growth Protocol

Spores were directly inoculated into 500 ml shake flasks containing 100 ml of either *Talaromyces* medium 1 or 2 and incubated at 45° C. at 250 rpm in an incubator shaker for 3-4 days.

Sample Preparation

For shake flask cultures, 3 ml of culture broth was transferred to a 12 ml disposable tube and centrifuged for 10 min at 5200 g. At least 1 ml of supernatant was harvested.

Protein Analysis

Protein samples were separated under reducing conditions on NuPAGE 4-12% Bis-Tris gel (Invitrogen, Breda, The Netherlands) and stained as indicated. Gels were stained with either InstantBlue (Expedeon, Cambridge, United Kingdom), SimplyBlue safestain (Invitrogen, Breda, The Netherlands) or Sypro Ruby (Invitrogen, Breda, The Netherlands)) according to manufacturer's instructions.

For Western blotting, proteins were transferred to nitrocellulose. The nitrocellulose filter was blocked with TBST (Tris buffered saline containing 0.1% Tween 40) containing 3% skim-milk and incubated for 16 hours with anti-FLAG M2 antibody (Sigma, Zwijndrecht, The Netherlands). Blots were washed twice with TBST for 10 minutes and stained with Horse-radish-peroxidase conjugated rabbit-anti-mouse antibody (DAKO, Glostrup, Denmark) for 1 hour. After washing the blots five times with TBST for 10 minutes, proteins were visualized using SuperSignal (Pierce, Rockford, U.S.A).

Wheat Straw Assay (WSU Assay).

Preparation of Pre-Treated, Washed Wheat Straw Substrate.

The washed wheat straw substrate was homogenised using an ultra-turrax, washed, lyophilized and grinded prior to analysis.

Measurement of Cellulase Activity in WSU/ml

Cellulase activity was herein measured in terms of "Wheat Straw Units" (WSU) per milliliter in a Wheat Straw assay (WSU assay). The washed wheat straw substrate was ultraturraxed, washed, lyophilized and grinded prior to analysis.

400 µl of supernatants harvested from shake flask experiments were diluted 16-fold. Duplicate, 200 µl samples were transferred to two suitable vials: one vial containing 700 µL 3% (w/w) dry matter of the pretreated, washed wheat straw substrate and 100 µl 250 mM citrate buffer, buffered at pH 4.5. The other vial consisted of a blank, where the 700 µl 3% (w/w) dry matter pretreated, washed wheat straw substrate was replaced by 700 µl water, with 100 µl 250 mM citrate buffer, buffered at pH 4.5. The assay samples are incubated for 20 and/or 60 hr at 65° C. After incubation of the assay samples, a fixed volume of $D_2O$ containing an internal standard, maleic acid is added. The amount of sugar released, is based on the signal between 5.25-5.20 ppm, relative to Dimethyl-sila-pentane-sulfonate determined by means of 1D $^1H$ NMR operating at a proton frequency of 500 MHz, using a pulse program with water suppression, at a temperature of 27° C. The cellulase enzyme solution may contain residual sugars. Therefore, the results of the assay are corrected for the sugar content of the enzyme solution.

Example 2

Overexpression of Multiple *Talaromyces emersonii* Cellulases in *Talaromyces emersonii*

Cloning of *T. emersonii* Genes in Expression Vectors

The genes encoding *T. emersonii* cellobiohydrolase-1 (CBI-II), *T. emersonii* beta-glucanase CEA (EG), and *T. emersonii* β-glucosidase (BG) were synthesised by DNA2.0 (Menlo Park, USA) and cloned as EcoRI/SnaBI fragment into the pGBTOP12 vector, comprising the glucoamylase promoter and terminator sequence, resulting in vector pGBTOPEBA205, pGBTOPEBA8 and pGBTOPEBA4, respectively. For cloning purposes, 198 nucleotides of the 3' part of the glucoamylase promoter was also synthesised with the genes. The amino acid sequences of the *T. emersonii* cellobiohydrolase-I (CBHI), *T. emersonii* beta-glucanase CEA (EG), and *T. emersonii* β-glucosidase (BG) are represented by SEQ ID NO: 1, 3, and 5, respectively. The DNA sequences of the genes are represented by SEQ ID NO: 2, 4 and 6, respectively. FIG. 7 represents a map of a pGBTOP-EBA205 containing the *T. emersonii* CBHI protein under control of the glaA promoter within vector pGBTOP12. pGBTOPEBA205 is representative for pGBTOPEBA8, which comprises *T. emersonii* EG, and pGBTOPEBA4, which comprises *T. emersonii* BG.

The gene encoding *T. emersonii* cellobiohydrolase-II (CBHII), was obtained from a *T. emersonii* cDNA library described in patent WO/2001/070998. FIG. 4 represents a map of pGBFINEBA176 containing the *T. emersonii* CBHII protein under control of the glaA promoter within vector pGBFIN11. The amino acid sequence and nucleotide sequence are represented by SEQ ID NO: 7 and 8, respectively.

Transformation of *emersonii* with Constructs Encoding Cellulases

Transformation of *T. emersonii* with constructs encoding cellulases was performed as described in EXAMPLE 1 of PCT/EP2010/066796. In total, 10 µg of DNA was used to co-transform *T. emersonii*: 1 µg of pAN8-1 and 2 µg of each of the vectors pGBTOPEBA4, pGBTOPEBA8, pGBTOPEBA205 and pGBFINEBA176.

Screening for Transformants Expressing all 4 Cellulases

Transformants were picked from plates and further grown into 96 wells microtiter plates (MTP) containing *Talaromyces* agar medium for 5 days at 40° C. The plates were replica plated using a 96-pin replicator into 96-well MTPs containing PDA medium. The MTP plates were incubated for 3 days at 40° C. and used to harvest spores for shake flask analysis. To do this, 100 µl of *Talaromyces* medium 1 was added to each well and after resuspending the mixture, 30 µl of spore suspension was used to inoculate 170 µl of *Talaromyces* medium 1 in MTP plates. The 96-well plates were incubated in humidity shakers (infors) for 44° C. at 550 rpm, and 80% humidity for 96 hours. Plunger plates were used to push down the mycelium and, subsequently, approximately 100 µl of supernatant was harvested per well.

Approximately 10 µl of supernatant was analysed for protein expression using the E-PAGE 96 Protein elecrophoresis system (Invitrogen, Breda, The Netherlands). Gels were stained with SimplyBlue protein staining and transformants expressing multiple cellulases were selected. Spores of interesting transformants were harvested from MTP master plates and used for spore batch preparations.

*T. emersonii* Shake Flask Fermentations and Sample Analysis

*T. emersonii* transformants expressing one or more cellulases were used for shake flask fermentations in *Talaromyces* medium 2 containing 5% of glucose. Analysis of protein expression by SDS-PAGE analysis was performed. Proteins were visualised using SYPRO Ruby protein staining.

The results of the SYPRO Ruby stained SOS-PAGE gel is presented in FIG. 4A. The different transformants expressed different combinations and expression levels of cellulases. The supernatant of transformant 20 (strain 20), contained all 4 cellulases, while, in contrast, no cellulase proteins were observed in the empty strain (FBG142). Therefore, multiple cellulases can simultaneously be overexpressed in T. emersonii in the presence of glucose.

Figure 4B:
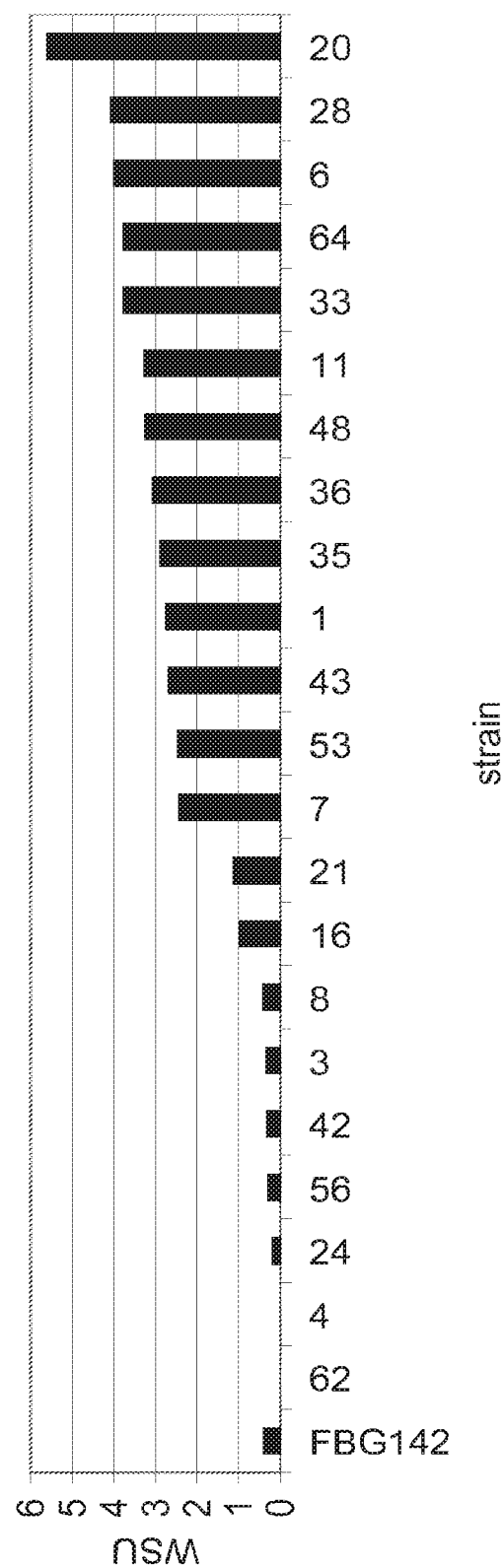

In order to test cellulase activity in T. emersonii transformants expressing one or more cellulases. WSU activity was measured in supernatants of an empty strain and the transformants. The results of the WSU assay is shown in FIG. 4B. In supernatants harvested after 72 hours from cultures of the empty strain grown in medium containing glucose no WSU activity could be measured. In contrast, in transformants a range of activities could be observed.

Transformant 20 expressing all 4 cellulases showed highest activity: almost 6 WSU/ml, or 5 WSU/ml or more. Transformants 20 and 28 had an activity of 4 WSU/ml or more, Transformants 20, 28, 6, 64, 33, 11 and 48 had an activity of 3 WSU/ml or more. Transformants 20, 28, 6, 64, 33, 11, 48, 36, 35 and 1 had an activity of 2.5 WSU/ml or more, and Transformants 20, 28, 6, 64, 33, 11, 48, 36, 35, 1, 43, 53 and 7 had an activity of 2 WSU/ml or more. All other transformants had an activity well below 1.5 WSU/ml.

To test whether transformant 20 also produced cellulase activity in the absence of an inducer, a shake flask fermentation was performed using *Talaromyces* medium 3. Supernatants were harvested at day 3, 4 and 5 and analysed for WSU activity. The results of the WSU assay are shown in Table 2.

TABLE 2

Results of WSU activity measurement in supernatants of an empty strain and *T. emersonii* transformant 20 in *Talaromyces* medium 3.

| Strain | cellulase activity (WSU/ml) | | |
| --- | --- | --- | --- |
| | Day 3 | Day 4 | Day 5 |
| Transformant 20 (multiple recombinant cellulases) | 6.1 | 7.7 | 8.1 |
| Empty strain | 0.0 | 0.4 | 0.9 |

No cellulase activity was observed in day 3 sups of an empty strain, while some activity was observed at later time-points. In contrast, the transformant overexpressing multiple cellulases under control of the glaA promoter showed WSU activity at day 3 (6.1 WSU/ml), and the activity further increased over time.

This experiment shows that *T. emersonii* transformants comprising multiple cellulases under control of the glaA promoter are able to produce cellulase activity in glucose containing medium with and without cellulose. The transformant can be obtained by screening a pool of transformants that have been transformed with 4 cellulase constructs.

The invention claimed is:

1. A process for preparing a fermentation product from a lignocellulosic material, said process comprising:
   (a) pretreatment of the lignocellulosic material;
   (b) contacting the pretreated lignocellulosic material with an enzyme composition comprising at least four different enzymes selected from the group consisting of cellulases, hemicellulases, and pectinases, said at least four different enzymes being produced and secreted by a transformed filamentous fungus host cell comprising at least four different heterologous polynucleotides encoding the at least four different enzymes, thereby producing at least one sugar; and
   (c) fermenting said sugar with a fermenting microorganism to produce said fermentation product.

2. The process for preparing a fermentation product according to claim 1, wherein the fermentation product is selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1, 3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulose, an amylase, a glucanase, a lactase, a lipase, a lyase, an oxidoreductase, a transferase or a xylanase.

3. The process of claim 1, wherein the enzyme composition comprises at least β-xylosidase.

4. The process of claim 1, wherein the enzyme composition comprises at least *Talaromyces* β-xylosidase.

5. The process of claim 1, wherein the enzyme composition comprises at least endoglucanase.

6. The process of claim 1, wherein the enzyme composition comprises at least *Talaromyces* endoglucanase.

7. The process of claim 6, wherein the endoglucanase has at least 90% identity with SEQ ID No. 3.

8. The process of claim 5, wherein EG is present in the enzyme composition at 12-70% of the total protein dose.

9. The process of claim 1, wherein the enzyme composition is unpurified fermentation broth.

10. The process of claim 1, wherein the enzyme composition is recovered from cultivation broth.

11. The process of claim 1, wherein the host cell is *Talaromyces*.

12. The process of claim 1, wherein the enzyme composition comprises a cellobiohydrolase I, a cellobiohydrolase II, a beta-glucosidase, an endoxylanase and an alpha-arabinofuranosidase.

13. The process of claim 1, wherein the lignocellulosic material is corn stover, corn kernels or fiber from kernels.

14. The process of claim 1, wherein the enzyme composition is contacted with lignocellulosic material that has a temperature in the range of from 60 to 80° C.

15. The process of claim 1, wherein the hydrolysis of the lignocellulosic material by the enzyme composition is performed at a temperature of 50 to 65° C.

16. The process of claim 1, which comprises a presaccharification step.

17. The process of claim 16, wherein the presaccharification step is performed from about 30° C. to 80° C. for 2 to 24 hours.

18. The process of claim 1, wherein the fermentation is performed under anaerobic conditions.

19. The process of claim 1, further comprising recovery of the fermentation product.

20. The process of claim 1, wherein the fermenting microorganism is a yeast.

21. The process of claim 1, wherein the fermenting microorganism ferments both xylose and glucose.

22. The process of claim 1, wherein the fermentation product is ethanol.

* * * * *

SEQUENCE LISTING

```
<160> NUMBER OF SEQ ID NOS: 16

<210> SEQ ID NO 1
<211> LENGTH: 455
<212> TYPE: PRT
<213> ORGANISM: Talaromyces emersonii
<220> FEATURE:
<221> NAME/KEY: MISC_FEATURE
<222> LOCATION: (1)..(455)
<223> OTHER INFORMATION: cellobiohydrolase I

<400> SEQUENCE: 1

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ser Asn Trp Arg Trp Val His Asn Val Gly Gly
    50                  55                  60

Tyr Thr Asn Cys Tyr Thr Gly Asn Thr Trp Asn Pro Thr Tyr Cys Pro
65                  70                  75                  80

Asp Asp Val Thr Cys Ala Glu Asn Cys Ala Leu Asp Gly Ala Asp Tyr
                85                  90                  95

Glu Gly Thr Tyr Gly Val Thr Ser Ser Gly Ser Glu Leu Arg Leu Asn
            100                 105                 110

Phe Val Thr Gly Ser Asn Val Gly Ser Arg Leu Tyr Leu Leu Gln Asp
        115                 120                 125

Asp Glu Thr Tyr Gln Ile Phe Lys Leu Leu Asn Arg Glu Phe Thr Phe
    130                 135                 140
```

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
            165                 170                 175

Lys Ala Gly Ala Lys Tyr Gly Thr Gly Tyr Cys Asp Ser Gln Cys Pro
        180                 185                 190

Arg Asp Leu Lys Phe Ile Asp Gly Glu Gly Asn Val Glu Gly Trp Gln
            195                 200                 205

Pro Ser Ser Asn Asn Ala Asn Thr Gly Ile Gly Asp His Gly Ser Cys
        210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Asp Gly Asp
            245                 250                 255

Asp Cys Gly Gly Thr Tyr Ser Thr Asn Arg Tyr Ala Gly Glu Cys Asp
        260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Gln Pro Phe Thr Val Val
        290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Gly Lys Val Ile Pro Gln Pro Asn
            325                 330                 335

Ser Asp Ile Ser Gly Val Thr Gly Asn Ser Ile Thr Thr Glu Phe Cys
        340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
        370                 375                 380

Val Met Ser Leu Trp Asp Asp Tyr Ala Ala Gln Met Leu Trp Leu Asp
385                 390                 395                 400

Ser Asp Tyr Pro Thr Asn Ala Ser Ala Thr Thr Pro Gly Val Ala Arg
            405                 410                 415

Gly Thr Cys Pro Thr Asp Ser Gly Val Pro Ser Gln Val Glu Ser Gln
        420                 425                 430

Ser Pro Asn Ser Tyr Val Thr Tyr Ser Asn Ile Lys Phe Gly Pro Ile
        435                 440                 445

Asn Ser Thr Phe Thr Ala Ser
    450                 455

<210> SEQ ID NO 2
<211> LENGTH: 1368
<212> TYPE: DNA
<213> ORGANISM: Artificial Sequence
<220> FEATURE:
<223> OTHER INFORMATION: T. emersonii CBHI

<400> SEQUENCE: 2
atgctccgcc gtgctcttct gctgagcagc tctgccatcc tggccgtcaa ggcccagcag     60
gctggtactg ccactgctga gaaccaccct cccttgacct ggcaggagtg cactgctcct    120
ggttcctgca ccactcagaa cggtgctgtt gtccttgaca gcaactggag atgggttcac    180
aacgtcggtg gttacaccaa ctgctacact ggcaacacct ggaaccccac ctactgcccc    240

```
gatgatgtca cctgcgctga gaactgcgct cttgacggtg ccgactacga gggtacctac      300
ggtgtcactt cttctggctc tgagctccgt ctgaacttcg tcaccggcag caacgtcggc      360
tctcgtctct acctcctcca ggatgacgag acctaccaga tcttcaagct cctcaaccgt      420
gagttcacct tcgatgttga tgtctccaac cttccttgcg gtctgaacgg tgctctgtac      480
ttcgtcgcca tggatgccga cggtggtgtc tccaagtacc caacaacaa ggccggtgcc       540
aagtacggta ctggctactg cgacagccag tgccccgtg acctcaagtt cattgacggc       600
gagggcaacg tcgagggctg gcagccctcc tccaacaacg ccaacactgg tatcggtgac      660
cacggctctt gctgcgctga gatggatgtc tgggaggcca actccatctc caacgccgtc      720
acccccacc cttgcgacac ccccggccag accatgtgcg atggtgatga ctgcggtggt       780
acctactcca ccaaccgcta cgccggtgag tgcgaccccg atggctgcga cttcaacccc      840
taccgcatgg gcaacacctc cttctacggc cctggcaaga tcattgacac cacccagccc      900
ttcaccgttg tcacccagtt cctgaccgat gacggcaccg acactggtac cctctccgag      960
atcaagcgct tctacatcca gaacggcaag gtcatccccc agcccaactc cgacatctcc     1020
ggtgtcaccg gcaactccat caccactgag ttctgcactg ctcagaagca ggctttcggt     1080
gacaccgatg acttctccca gcacggtggt cttgccaaga tgggtgctgc catgcagcag     1140
ggtatggtcc tggtcatgtc cctctgggat gactacgctg ctcagatgct ctggctcgac     1200
tccgactacc ccaccaacgc ctccgccacc actcctggtg ttgctcgtgg tacctgcccc     1260
accgactctg gtgttcctag ccaggttgag agccagtccc ccaactccta cgtgacctac     1320
tccaacatca gttccggtcc catcaactcc accttcactg catcgtaa                  1368
```

<210> SEQ ID NO 3
<211> LENGTH: 335
<212> TYPE: PRT
<213> ORGANISM: Talaromyces emersonii
<220> FEATURE:
<221> NAME/KEY: MISC_FEATURE
<222> LOCATION: (1)..(335)
<223> OTHER INFORMATION: beta-glucanase CEA

<400> SEQUENCE: 3

```
Met Lys Phe Ser Arg Val Val Cys Gly Leu Thr Ala Ala Gly Gly Ala
1               5                   10                  15

Leu Ala Ala Pro Val Lys Glu Lys Gly Ile Lys Lys Arg Ala Ser Pro
            20                  25                  30

Phe Gln Trp Phe Gly Ser Asn Glu Ser Gly Ala Glu Phe Gly Asn Asn
        35                  40                  45

Asn Ile Pro Gly Val Glu Gly Thr Asp Tyr Thr Phe Pro Asn Thr Ser
    50                  55                  60

Ala Ile Gln Ile Leu Asp Gln Gly Met Asn Ile Phe Arg Val Pro
65                  70                  75                  80

Phe Leu Met Glu Arg Met Val Pro Asn Gln Met Thr Gly Pro Val Asp
                85                  90                  95

Ser Ala Tyr Phe Gln Gly Tyr Ser Gln Val Ile Asn Tyr Ile Thr Ser
            100                 105                 110

His Gly Ala Ser Ala Val Ile Asp Pro His Asn Phe Gly Arg Tyr Tyr
        115                 120                 125

Asn Asn Ile Ile Ser Ser Pro Ser Asp Phe Gln Thr Phe Trp His Thr
    130                 135                 140

Ile Ala Ser Asn Phe Ala Asp Asn Asp Asn Val Ile Phe Asp Thr Asn
145                 150                 155                 160
```

```
Asn Glu Tyr His Asp Met Asp Glu Ser Leu Val Val Gln Leu Asn Gln
            165                 170                 175
Ala Ala Ile Asp Gly Ile Arg Ala Ala Gly Ala Thr Ser Gln Tyr Ile
        180                 185                 190
Phe Val Glu Gly Asn Ser Trp Thr Gly Ala Trp Thr Trp Thr Gln Val
    195                 200                 205
Asn Asp Ala Met Ala Asn Leu Thr Asp Pro Gln Asn Lys Ile Val Tyr
210                 215                 220
Glu Met His Gln Tyr Leu Asp Ser Asp Gly Ser Gly Thr Ser Asp Gln
225                 230                 235                 240
Cys Val Asn Ser Thr Ile Gly Gln Asp Arg Val Glu Ser Ala Thr Ala
            245                 250                 255
Trp Leu Lys Gln Asn Gly Lys Lys Ala Ile Leu Gly Glu Tyr Ala Gly
        260                 265                 270
Gly Ala Asn Ser Val Cys Glu Thr Ala Val Thr Gly Met Leu Asp Tyr
    275                 280                 285
Leu Ala Asn Asn Thr Asp Val Trp Thr Gly Ala Ile Trp Trp Ala Ala
    290                 295                 300
Gly Pro Trp Trp Gly Asp Tyr Ile Phe Ser Met Glu Pro Pro Ser Gly
305                 310                 315                 320
Ile Ala Tyr Glu Gln Val Leu Pro Leu Leu Lys Pro Tyr Leu Glu
            325                 330                 335

<210> SEQ ID NO 4
<211> LENGTH: 1008
<212> TYPE: DNA
<213> ORGANISM: Artificial Sequence
<220> FEATURE:
<223> OTHER INFORMATION: T. emersonii beta-glucanase

<400> SEQUENCE: 4
atgaagttct ctcgtgttgt ctgcggtctg accgctgctg gtggtgctct tgctgctcct      60
gtcaaggaga agggtatcaa gaagcgtgcc tcccccttcc agtggttcgg ttccaacgag     120
agcggtgctg agttcggcaa caacaacatc cccggtgttg agggtaccga ctacaccttc     180
cccaacactt ctgccatcca gatcctgatt gaccagggca tgaacatctt ccgtgtcccc     240
ttcctgatgg agcgcatggt tcccaaccag atgactggtc tgttgactc tgcctacttc     300
cagggctact ctcaggtcat caactacatc acctcccacg gtgcctccgc cgtcattgac     360
cctcacaact cggccgcta ctacaacaac atcatctcct cccctccga cttccagacc      420
ttctggcaca ccattgcctc caacttcgcc gacaacgaca cgtcatctt cgacaccaac     480
aacgagtacc acgacatgga tgagagcttg gttgtccagc tcaaccaggc tgccattgat     540
ggtatccgtg ctgctggtgc caccagccag tacatcttcg tcgagggcaa cagctggact     600
ggtgcctgga cctggaccca ggtcaacgat gccatggcca acctgaccga cccccagaac     660
aagatcgtct acgagatgca ccagtacctc gactccgacg gcagcggtac ctccgaccag     720
tgcgtcaact ccaccattgg ccaggaccgt gttgagtctg ccactgcctg gctcaagcag     780
aacggcaaga aggccatcct gggtgaatac gctggtggtg ccaactccgt ctgcgagact     840
gctgtcaccg gcatgcttga ctacctcgcc aacaacaccg atgtctggac tggtgccatc     900
tggtgggctg ctggtccctg gtggggtgac tacatcttct ccatggagcc tccctccggc     960
attgcctacg agcaggtcct tcctctcctc aagccctacc tcgaataa               1008
```

```
<210> SEQ ID NO 5
<211> LENGTH: 857
<212> TYPE: PRT
<213> ORGANISM: Talaromyces emersonii
<220> FEATURE:
<221> NAME/KEY: MISC_FEATURE
<222> LOCATION: (1)..(857)
<223> OTHER INFORMATION: beta-glucosidase

<400> SEQUENCE: 5

Met Arg Asn Gly Leu Leu Lys Val Ala Ala Leu Ala Ala Ala Ser Ala
 1               5                  10                  15

Val Asn Gly Glu Asn Leu Ala Tyr Ser Pro Pro Phe Tyr Pro Ser Pro
             20                  25                  30

Trp Ala Asn Gly Gln Gly Asp Trp Ala Glu Ala Tyr Gln Lys Ala Val
         35                  40                  45

Gln Phe Val Ser Gln Leu Thr Leu Ala Glu Lys Val Asn Leu Thr Thr
     50                  55                  60

Gly Thr Gly Trp Glu Gln Asp Arg Cys Val Gly Gln Val Gly Ser Ile
 65                  70                  75                  80

Pro Arg Leu Gly Phe Pro Gly Leu Cys Met Gln Asp Ser Pro Leu Gly
                 85                  90                  95

Val Arg Asp Thr Asp Tyr Asn Ser Ala Phe Pro Ala Gly Val Asn Val
            100                 105                 110

Ala Ala Thr Trp Asp Arg Asn Leu Ala Tyr Arg Arg Gly Val Ala Met
        115                 120                 125

Gly Glu Glu His Arg Gly Lys Gly Val Asp Val Gln Leu Gly Pro Val
    130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
            180                 185                 190

Leu Tyr Glu Gln Glu His Phe Arg Gln Gly Ala Gln Asp Gly Tyr Asp
        195                 200                 205

Ile Ser Asp Ser Ile Ser Ala Asn Ala Asp Asp Lys Thr Met His Glu
    210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
            260                 265                 270

Phe Val Met Thr Asp Trp Gly Gly His His Ser Gly Val Gly Ser Ala
        275                 280                 285

Leu Ala Gly Leu Asp Met Ser Met Pro Gly Asp Ile Ala Phe Asp Ser
    290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
            340                 345                 350

Asp Ser Trp Thr Leu Asp Thr Tyr Gly Pro Glu His Tyr Ala Val Gly
        355                 360                 365
```

```
Gln Gly Gln Thr Lys Ile Asn Glu His Val Asp Val Arg Gly Asn His
        370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                    405                 410                 415

Phe Gly Lys Asp Ala Gly Ser Asn Pro Trp Gly Val Asn Gly Cys Ser
                420                 425                 430

Asp Arg Gly Cys Asp Asn Gly Thr Leu Ala Met Gly Trp Gly Ser Gly
            435                 440                 445

Thr Ala Asn Phe Pro Tyr Leu Val Thr Pro Gln Ala Ile Gln Arg
        450                 455                 460

Glu Val Leu Ser Arg Asn Gly Thr Phe Thr Gly Ile Thr Asp Asn Gly
465                 470                 475                 480

Ala Leu Ala Glu Met Ala Ala Ala Ser Gln Ala Asp Thr Cys Leu
                485                 490                 495

Val Phe Ala Asn Ala Asp Ser Gly Glu Gly Tyr Ile Thr Val Asp Gly
                500                 505                 510

Asn Glu Gly Asp Arg Lys Asn Leu Thr Leu Trp Gln Gly Ala Asp Gln
            515                 520                 525

Val Ile His Asn Val Ser Ala Asn Cys Asn Asn Thr Val Val Leu
        530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Lys Thr Pro
                580                 585                 590

Phe Thr Trp Gly Arg Ala Arg Asp Asp Tyr Gly Ala Pro Leu Ile Val
            595                 600                 605

Lys Pro Asn Asn Gly Lys Gly Ala Pro Gln Gln Asp Phe Thr Glu Gly
            610                 615                 620

Ile Phe Ile Asp Tyr Arg Arg Phe Asp Lys Tyr Asn Ile Thr Pro Ile
625                 630                 635                 640

Tyr Glu Phe Gly Phe Gly Leu Ser Tyr Thr Thr Phe Glu Phe Ser Gln
                645                 650                 655

Leu Asn Val Gln Pro Ile Asn Ala Pro Pro Tyr Thr Pro Ala Ser Gly
                660                 665                 670

Phe Thr Lys Ala Ala Gln Ser Phe Gly Gln Pro Ser Asn Ala Ser Asp
            675                 680                 685

Asn Leu Tyr Pro Ser Asp Ile Glu Arg Val Pro Leu Tyr Ile Tyr Pro
            690                 695                 700

Trp Leu Asn Ser Thr Asp Leu Lys Ala Ser Ala Asn Asp Pro Asp Tyr
705                 710                 715                 720

Gly Leu Pro Thr Glu Lys Tyr Val Pro Pro Asn Ala Thr Asn Gly Asp
                725                 730                 735

Pro Gln Pro Ile Asp Pro Ala Gly Gly Ala Pro Gly Gly Asn Pro Ser
            740                 745                 750

Leu Tyr Glu Pro Val Ala Arg Val Thr Thr Ile Ile Thr Asn Thr Gly
            755                 760                 765

Lys Val Thr Gly Asp Glu Val Pro Gln Leu Tyr Val Ser Leu Gly Gly
770                 775                 780
```

```
Pro Asp Asp Ala Pro Lys Val Leu Arg Gly Phe Asp Arg Ile Thr Leu
785                 790                 795                 800

Ala Pro Gly Gln Gln Tyr Leu Trp Thr Thr Thr Leu Thr Arg Arg Asp
            805                 810                 815

Ile Ser Asn Trp Asp Pro Val Thr Gln Asn Trp Val Val Thr Asn Tyr
        820                 825                 830

Thr Lys Thr Ile Tyr Val Gly Asn Ser Ser Arg Asn Leu Pro Leu Gln
    835                 840                 845

Ala Pro Leu Lys Pro Tyr Pro Gly Ile
    850                 855

<210> SEQ ID NO 6
<211> LENGTH: 2574
<212> TYPE: DNA
<213> ORGANISM: Artificial Sequence
<220> FEATURE:
<223> OTHER INFORMATION: T. emersonii beta-glucosidase

<400> SEQUENCE: 6
atgcgcaacg gtctgctcaa ggttgctgct cttgctgctg cctccgccgt caacggcgag      60
aacctggcct actctcctcc cttctacccc tcccccctggg ccaacggcca gggtgactgg    120
gctgaggcct accagaaggc cgtccagttc gtcagccagc tcaccctggc tgagaaggtc    180
aacctgacca ctggtactgg ctgggagcag gaccgctgcg ttggccaggt cggctccatc    240
ccccgtcttg gtttccccgg tctttgcatg caggactctc ctcttggtgt ccgtgacacc    300
gactacaact ctgcttttcc tgctggtgtc aacgtcgctg ccacctggga ccgcaacctg    360
gcctaccgcc gtggtgttgc catgggtgag gagcaccgtg gcaagggtgt tgatgtccag    420
ctcggtcctg ttgctggtcc tctgggccgc tctcccgatg ctggccgcaa ctggaggggt    480
ttcgctcctg accccgtcct cactggtaac atgatggcct ccaccatcca gggtatccag    540
gatgctggtg tcattgcctg cgccaagcac ttcatcctgt acgagcagga gcacttccgc    600
cagggtgctc aggatggcta cgatatatct gactccatct ccgccaacgc cgatgacaag    660
accatgcacg agctctacct ctggcccttc gccgatgccg tcgtgctggg tgttggctcc    720
gtcatgtgct cctacaacca ggtcaacaac tcctacgcct gctccaacag ctacaccatg    780
aacaagctct tgaaatcaga gcttggtttc cagggttcg tcatgactga ctggggtggt    840
caccactctg tgttggttc cgctcttgct ggtcttgaca tgagcatgcc cggtgacatt    900
gctttcgact ccggtacctc cttctggggt accaacctga ccgttgccgt cctcaacggc    960
agcatccccg aatggcgtgt cgatgacatg gccgtccgta tcatgtctgc ctactacaag   1020
gtcggtcgtg accgctactc cgtccccatc aacttcgaca gctggaccct cgacacctac   1080
ggccctgagc actacgccgt cggccagggt cagaccaaga tcaacgagca cgttgatgtc   1140
cgtggcaacc acgctgagat catccacgag atcggtgctg cctccgccgt cctcctcaag   1200
aacaagggtg tcctgccctt gactggtact gagcgcttcg tcggtgtgtt cggcaaggat   1260
gccggttcca ccccctgggg tgtcaacggc tgctccgacc gtggctgcga caacggcacc   1320
ctcgccatgg gctggggcag cggtactgcc aacttcccct acctggtcac ccccgagcag   1380
gccatccagc gtgaggtcct ttctcgcaac ggcaccttca ctggtatcac cgacaacggt   1440
gctcttgctg agatggctgc tgctgcctcc caggccgaca cctgcctggt ctttgccaac   1500
gccgacagcg gtgagggcta catcaccgtt gacggcaacg agggtgaccg caagaacctg   1560
accctctggc agggtgccga ccaggtcatc cacaacgttt ccgccaactg caacaacact   1620
```

```
gttgttgtcc tccacaccgt cggtcctgtc ctgattgatg actggtacga ccaccccaac    1680
gtcactgcca tcctctgggc tggtctgccc ggtcaggagt ccggcaactc gctagttgat    1740
gtcctctacg ccgtgtcaa ccccggcaag actcccttca cctggggtcg tgctcgtgat    1800
gactacggtg ctcctctgat tgtcaagccc aacaacggca agggtgctcc tcagcaggac    1860
ttcaccgagg gtatcttcat tgactaccgc cgcttcgaca agtacaacat caccccatc     1920 tacgagttcg gtttcggtct gagctacacc accttcgagt ctcccagct caacgtccag     1980 cccatcaacg ctcctcccta cactcccgcc tccggtttca ccaaggctgc tcagtccttc    2040
ggccagccct ccaacgcctc cgacaacctc taccctccg acattgagcg tgttcctctg     2100
tacatctacc cctggctcaa cagcactgac ctcaaggcct ctgccaacga ccccgactac    2160
ggccttccta ctgagaagta cgtgcctccc aacgccacca cggtgaccc ccagcccatt     2220 gaccctgctg gtggtgctcc tggtggcaac ccctccctct acgagcctgt tgctcgtgtc    2280
accaccatca tcaccaacac tggcaaggtc actggtgatg aggttcctca gctctacgtc    2340
agccttggtg gtcccgatga tgctcccaag gtcctccgtg gtttcgaccg tatcaccctg    2400
gctcctggcc agcagtacct ctggaccacc accctcaccc gccgtgacat ctccaactgg    2460
gaccccgtca cccagaactg ggttgtcacc aactacacca gaccatcta cgtcggcaac    2520 agctctcgca acctgcccct ccaggctcct ctcaagccct accccggcat ataa          2574

<210> SEQ ID NO 7
<211> LENGTH: 459
<212> TYPE: PRT
<213> ORGANISM: Talaromyces emersonii
<220> FEATURE:
<221> NAME/KEY: MISC_FEATURE
<222> LOCATION: (1)..(459)
<223> OTHER INFORMATION: cellobiohydrolase II

<400> SEQUENCE: 7
```

Met Arg Asn Leu Leu Ala Leu Ala Pro Ala Ala Leu Leu Gly Ala
1               5                   10                  15

Ala Asp Ala Gln Gln Ser Leu Trp Gly Gln Cys Gly Gly Asn Ser Trp
            20                  25                  30

Thr Gly Ala Thr Asp Cys Ala Ala Gly Ala Thr Cys Ser Thr Ile Asn
        35                  40                  45

Ser Tyr Tyr Ala Gln Cys Val Pro Ala Thr Ala Thr Pro Thr Thr Leu
    50                  55                  60

Thr Thr Thr Thr Lys Pro Ser Ser Thr Ala Pro Thr Thr Pro Pro Pro
65                  70                  75                  80

Thr Ser Ala Thr Thr Thr Gly Thr Gly Ser Ala Thr Ser Pro Ser Ile
                85                  90                  95

Thr Ala Ser Ala Ser Gly Asn Pro Phe Val Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Asn Met Gly Glu Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

```
Ala Ala Ser Asn Gly Glu Phe Ser Ile Ala Asn Asn Gly Val Ala Leu
            195                 200                 205

Tyr Lys Gln Tyr Ile Asp Ser Ile Arg Glu Gln Leu Thr Thr Tyr Ser
        210                 215                 220

Asp Val His Thr Ile Leu Ile Glu Pro Asp Ser Leu Ala Asn Leu
225                 230                 235                 240

Val Thr Asn Leu Asn Val Ala Lys Cys Ala Asn Ala Gln Gly Ala Tyr
                245                 250                 255

Leu Glu Cys Ile Asn Tyr Ala Ile Thr Gln Leu Asn Leu Pro Asn Val
            260                 265                 270

Ala Met Tyr Leu Asp Ala Gly His Ala Gly Trp Leu Gly Trp Ser Ala
        275                 280                 285

Asn Leu Gln Pro Ala Ala Gln Leu Phe Ala Glu Val Tyr Lys Asn Ala
    290                 295                 300

Ser Ser Pro Ala Ser Val Arg Gly Leu Ala Thr Asn Val Ala Asn Tyr
305                 310                 315                 320

Asn Ala Trp Thr Ile Ser Pro Cys Pro Ser Tyr Thr Gln Gly Asp Pro
                325                 330                 335

Asn Cys Asp Glu Glu Asp Tyr Val Asn Ala Leu Ala Pro Leu Leu Gln
            340                 345                 350

Ser Gln Gly Phe Asn Ala Tyr Phe Ile Thr Asp Thr Ser Arg Asn Gly
        355                 360                 365

Val Gln Pro Thr Lys Gln Asn Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Pro Phe
    450                 455

<210> SEQ ID NO 8
<211> LENGTH: 1380
<212> TYPE: DNA
<213> ORGANISM: Talaromyces emersonii
<220> FEATURE:
<221> NAME/KEY: misc_feature
<222> LOCATION: (1)..(1380)
<223> OTHER INFORMATION: cellobiohydrolase II

<400> SEQUENCE: 8
atgcgaaatc tgcttgctct tgcaccggca gcgctgcttc tcggcgcagc ggacgcgcaa      60
caatccctct ggggacaatg cggagggaat tcgtggactg agcgacggga ttgtgctgca     120
ggagcgacgt gcagcaccat caattcttac tacgcacaat gcgtccctgc aacggccact     180
cctaccacgt tgacgacaac gacaaagccc tcgtcgactg cgccaacgac ccctcctccg     240
acgtcagcga cgaccacagg cactggatcg gcgacatcgc cctccatcac gcgtctgcg      300 tccggcaacc cctttgtcgg ataccagctc tacgccaacc gtactatgc ctctgaggtg      360 attagcctgg ccatcccgtc gctaagcagc gagctggttc ccaaggcgag cgaggtggcc     420
aaggtgccgt cttttgtctg gctcgatcaa gcggccaaag tgcccaacat gggcgagtat     480
```

```
ctgaaagaca tccagtccca gaatgcggcc ggcgcagacc ctccgattgc aggcatcttc      540
gtcgtttacg acctacctga ccgcgactgc cggcggcag cgagcaatgg cgagttctcc       600
atcgccaaca acggcgttgc cctgtacaag caatacatcg actcgatccg cgagcagctg      660
acgacgtatt cggatgtgca caccatcctg atcattgaac ccgacagcct ggccaacctg      720
gtcaccaacc tgaacgtggc gaaatgcgcg aatgcccagg cgcctatct cgaatgcatc       780 aactacgcca tcacgcagct caacctgccg aatgtggcca tgtatcttga tgctggacac     840
gccggatggc taggctggtc agcaaaacctc caacccgctg cgcagctgtt tgcagaggtc    900
tacaagaacg cctcgtcgcc ggcctcggtg cgcggtctcg cgaccaacgt cgccaactac     960
aacgcctgga cgatcagccc gtgcccgtcg tacacgcagg gcgaccccaa ctgcgacgag    1020
gaggactatg tgaatgccct tgcgccgctg cttcagagcc agggggttaa tgcgtacttt    1080
atcactgata catcccgcaa cggcgtccaa cccaccaagc agaaccaatg gggcgactgg    1140
tgcaacgtca tcggcaccgg gttcggcgtc cgcccgacga ctgacactgg caaccctctc    1200
gaggacgcct tcgtctgggt caagccgggt ggcgagagcg atggcacgtc taacacgacc    1260
tctccgcgat acgactacca ctgcgggctg agcgatgcgc tgcagccggc tccggaggcg    1320
ggaacttggt tccaggcgta ctttgagcag ctgcttacga atgccaatcc gccgttctga    1380
```

<210> SEQ ID NO 9
<211> LENGTH: 209
<212> TYPE: PRT
<213> ORGANISM: Talaromyces emersonii
<220> FEATURE:
<221> NAME/KEY: MISC_FEATURE
<222> LOCATION: (1)..(209)
<223> OTHER INFORMATION: unknown protein

<400> SEQUENCE: 9

```
Met Lys Gln Thr Ala Val Leu Pro Ile Leu Pro Ile Leu Phe Thr Thr
1               5                   10                  15

Ala Arg Ala Gly Asn Ile Leu Trp Ser Gly Ile Phe Asn Ser Ser Val
            20                  25                  30

Thr Val Ala Asp Phe Asp Leu Trp Ser Trp Ser Asn Gln Ile Glu Pro
        35                  40                  45

Trp Gln Trp Tyr Ile His Gly Ser Gly Pro Thr Ser Glu Tyr Leu Gly
    50                  55                  60

Leu Ser Pro Asp Phe Lys Asn Pro Ala Asp Thr Ser Asp Ala Gln Gly
65                  70                  75                  80

Ile Arg Ile Thr Ile Ser His Phe Thr Glu Ile Lys Tyr Gly Thr Leu
                85                  90                  95

Ser Gly Gln Thr Ala Pro Asp Asn Thr Leu Arg Trp Asp Val Gln Ser
            100                 105                 110

Val Thr Gln Trp Ser Thr Gln Leu Val Pro Asp Asn Trp Tyr Asn Phe
        115                 120                 125

Ala Tyr Asp Ile Asp Phe Asp Ala Gly Thr Val Gly Leu Trp Ala Ser
    130                 135                 140

Asn Gly Ser Asp Pro Leu Gln Gln Val Val Ala Pro Ile Ser Ala Ala
145                 150                 155                 160

Thr Ser Thr Asn Ser Glu Asp Trp His Val Gly Leu Arg Leu Pro
                165                 170                 175

Asn Gly Gly Ser Asp Pro Ala Pro Glu Asp Trp Tyr Trp Ser Gly Ile
            180                 185                 190
```

```
Trp Ile Glu Gln Ala Pro Ile Thr Thr Ser Ile Ala Gly Pro Leu Ala
            195                 200                 205

Ser
```

<210> SEQ ID NO 10
<211> LENGTH: 630
<212> TYPE: DNA
<213> ORGANISM: Artificial Sequence
<220> FEATURE:
<223> OTHER INFORMATION: Talaromyces emersoni unknown protein (DNA coding region)

<400> SEQUENCE: 10

```
atgaagcaga cagcagtcct ccccattctt ccaatcctct tcaccaccgc tcgcgcgggc      60
aatatcctct ggagcggaat cttcaattcc tccgtcacgg ttgcggactt tgatttgtgg     120
tcctggtcca accagatcga gccatggcaa tggtacatcc acggcagtgg gccgacgagc     180
gagtatctgg gtctgtcgcc tgatttcaag aatccagcgg atacgagcga tgcgcagggc     240
ataaggatta caattagcca cttcaccgaa ataaaatacg gcacgctgag cggacaaacc     300
gccccggata cacgctgcg ctgggacgtg caatccgtca cgcagtggtc gacgcaactg      360
gtgccagaca actggtacaa cttttgcgtac gacatcgact cgacgcgggg gaccgtcggc    420
ctctgggcgt ccaacggctc ggatccgctg cagcaggtcg tggcgcccat cagcgcggcg     480
acgtcgacca attctgaaga ctggcacgtc ggcgagttgc gtttgcccaa cggtggttcg     540
gacccggcgc ctgaggactg gtactggtct ggtatttgga ttgagcaggc tcctattacg     600
acgagcattg cggggccgtt ggctagctaa                                      630
```

<210> SEQ ID NO 11
<211> LENGTH: 632
<212> TYPE: PRT
<213> ORGANISM: Talaromyces emersonii
<220> FEATURE:
<221> NAME/KEY: MISC_FEATURE
<222> LOCATION: (1)..(632)
<223> OTHER INFORMATION: Swollenin

<400> SEQUENCE: 11

```
Met Gln Val Ser Arg Ile Ala Ala Leu Ala Ala Leu Leu Gln Gly Ala
1               5                   10                  15

Trp Ala Gln Ala Gly Pro Tyr Ala Gln Cys Gly Gly Leu Gly Tyr Ser
            20                  25                  30

Gly Ser Thr Val Cys Thr Ala Gly Tyr Ile Cys Thr Ser Gln Asn Pro
        35                  40                  45

Tyr Tyr Tyr Gln Cys Val Pro Ala Thr Ala Thr Thr Ile Ala Ala
    50                  55                  60

Thr Thr Thr Thr Ser Pro Ala Ser Ala Ser Ser Thr Ser Thr Ala Pro
65                  70                  75                  80

Ser Thr Thr Cys Thr Gly Thr Phe Thr Pro Ile Ser Ala Ala Asp Phe
                85                  90                  95

Val Ala Asn Leu Asn Pro Gly Trp Asn Leu Gly Asn Thr Leu Asp Ala
            100                 105                 110

Ile Pro Asp Glu Gly Ser Trp Asn Asn Pro Val Val Pro Leu Thr
        115                 120                 125

Phe Asp Asp Val Lys Ala Ala Gly Phe Lys Ser Val Arg Leu Pro Val
    130                 135                 140

Thr Tyr Ala Tyr His Phe Val Gly Gly Ser Pro Asp Trp Thr Ile Asn
145                 150                 155                 160
```

```
Ala Thr Trp Leu Gln Arg Val Ser Asp Val Val Asp Met Ile Thr Ser
                165                 170                 175

Arg Gly Leu Tyr Ala Ile Val Asn Ala His His Asp Ser Trp Ile Trp
            180                 185                 190

Ala Asp Val Thr Gln Pro Gly Ala Asn Leu Thr Met Ile Glu Glu Lys
        195                 200                 205

Phe Tyr Arg Leu Trp Tyr Gln Val Gly Ser Lys Leu Ala Cys Lys Ser
    210                 215                 220

Ser Leu Val Ala Phe Glu Pro Ile Asn Glu Pro Pro Cys Asn Asp Ala
225                 230                 235                 240

Thr Asp Ala Ala Glu Ile Asn Lys Leu Asn Ala Ile Phe Leu Lys Ala
                245                 250                 255

Ile Asn Asp Ala Gly Phe Asn Ala Gln Arg Val Val Thr Leu Val
            260                 265                 270

Gly Gly Gly Glu Asp Ser Val Lys Thr Ser Glu Trp Phe Val Ala Pro
        275                 280                 285

Thr Gly Tyr Pro Asn Pro Tyr Ala Ile Gln Phe His Tyr Tyr Asn Pro
    290                 295                 300

Tyr Asp Phe Ile Phe Ser Ala Trp Gly Lys Thr Ile Trp Gly Ser Glu
305                 310                 315                 320

Ser Asp Lys Ser Ala Leu Ser Thr Asp Leu Gln Leu Ile Arg Asn Asn
                325                 330                 335

Phe Thr Thr Val Pro Leu Leu Ile Gly Glu Tyr Asp Ala Ser Pro Thr
            340                 345                 350

Asn Cys Glu Thr Ala Ala Arg Trp Lys Tyr Phe Asp Tyr Phe Ile Arg
        355                 360                 365

Thr Ala Ser Ala Leu Asn Ile Ser Thr Ile Leu Trp Asp Asn Gly Gly
    370                 375                 380

Asp His Leu Asp Arg Thr Thr Gly Thr Trp Arg Asp Pro Ser Ala Ile
385                 390                 395                 400

Asn Ile Ile Met Asp Ala Thr Gly Gly Ile Thr Asn Ser Leu Pro Asp
                405                 410                 415

Ser Thr Glu Asp Pro Ser Ala Thr Thr Gln Trp Ser Ser Ala Tyr Ile
            420                 425                 430

Phe His Lys Tyr Gly Asp Pro Val Ser Asp Gln Ser Leu Pro Phe Leu
        435                 440                 445

Phe Asn Gly Asn Ser Val Ser Ser Ile Ser Ala Ser Asp Gly Thr Lys
    450                 455                 460

Leu Thr Ala Asp Thr Asp Tyr Val Val Ala Gly Ser Asn Ile Thr Phe
465                 470                 475                 480

Lys Ala Ser Phe Leu Ser Lys Tyr Leu Ser Ser Thr Thr Ala Pro Gly
                485                 490                 495

Ile Leu Ala Asn Leu Thr Val Ser Phe Ser Ala Gly Ala Ser Glu Val
            500                 505                 510

Ile Gln Leu Val Gln Trp Lys Thr Pro Ser Leu Ser Ser Thr Ser Ala
        515                 520                 525

Val Ala Ser Ala Val Asn Gly Ser Asp Leu Tyr Ile Pro Ile Thr Trp
    530                 535                 540

Gly Gly Ile Pro Lys Pro Ala Ala Val Lys Ala Val Glu Ala Asn Gly
545                 550                 555                 560

Asn Tyr Leu Val Asp Ser Trp Thr Glu Tyr Leu Pro Ala Ile Gln Gln
                565                 570                 575
```

Gly Arg Thr Thr Tyr Ser Ser Gln Trp Asn Trp Asp Asp Ser His Val
            580                 585                 590

Ile Ile Thr Ala Ala Thr Ile Ser Asp Val Leu Ala Ala Gly Gln Thr
        595                 600                 605

Thr Val Phe Thr Phe Glu Phe Tyr Pro Arg Asp Asn Gly Val Val Asn
    610                 615                 620

Ala Val Asn Phe Thr Leu Thr Val
625                 630

<210> SEQ ID NO 12
<211> LENGTH: 1932
<212> TYPE: DNA
<213> ORGANISM: Artificial Sequence
<220> FEATURE:
<223> OTHER INFORMATION: Talaromyces emersoni Swollenin (DNA coding
      region)

<400> SEQUENCE: 12

```
atgcaggtct ctcgtatcgc tgcacttgct gccctcctgc agggtgcctg ggcacaagca      60
ggcccctacg ctcagtgcgg cggactcggc tattcaggaa gcaccgtctg cactgcaggt     120
tatatctgca cttcacagaa tccttattat tatcagtgtg tcccggcaac agcaacgact     180
acaatcgcag caacgactac aacctcgcct gcttcagcat cctccacttc cactgcccct     240
tcgaccactt gcactgggac gttcacgccc atctcagccg ccgactttgt cgccaatctc     300
aatcccggat ggaacttggg aaacacactc gatgcaatcc ccgacgaagg gtcatggaat     360
aatcctcccg ttgtgccgtt gacgtttgac gatgtgaaag cggcgggttt caagagcgtc     420
agacttccag tcacctatgc atatcacttt gtaggtggct ccctgactg gaccatcaac      480
gcgacatggc tgcagagggt atccgacgtg gttgacatga tcacatcccg cgggttgtac     540
gccatcgtca acgctcatca cgactcgtgg atctgggcgg acgtaaccca gccaggcgca     600
aatctgacca tgatcgagga aaagttctac cgtctctggt accaagtagg cagcaagctg     660
gcgtgcaagt ccagcctggt cgcattcgag cccatcaacg aaccgccctg caacgatgcg     720
actgacgccg ccgaaaatca aaagctgaat gccatcttcc tgaaggcaat caacgatgcc     780
ggcggattca atgcccagcg cgtggtgacc ctcgttggtg gcggcgagga cagcgtcaag     840
acatcggagt ggttcgtggc gccgacgggg tatccgaatc cttatgcgat tcagttccac     900
tactacaatc cttatgattt tattttcagc gcatggggca agacgatctg gggctcagaa     960
tccgacaaat ccgccctgtc gaccgatctc caactgatcc gaaacaactt cactaccgtt    1020
cctcttctga tcggagaata cgatgcgtcc ccgacaaact cgaaacggc cgcgcggtgg     1080
aagtacttcg actatttcat ccgcaccgct agcgcgctca acatatcaac catcctgtgg    1140
gataacggtg gagatcatct cgaccgtacg accggcacct ggcgcgatcc atctgccatc    1200
aacatcatca tggacgcaac cgggggaatc accaacagcc tgcccgacag cacggaggat    1260
ccgagcgcga cgacgcagtg gtcgtccgcg tacatcttcc acaaatacgg ggatccggtc    1320
agcgatcaga gtctcccgtt cctgttcaac gggaactccg tttcgtcgat cagtgcgtcg    1380
gacgggacga aattaacggc tgatacggac tacgtcgttg ccggctcgaa tatcacattc    1440
aaggcgtcgt tcctctcgaa ataccctctct tcgacaaccg cgcccgggcat tctcgccaat    1500
ctgaccgtga gcttctctgc gggtgcttcg gaggtgatcc agctcgtgca gtggaaaacg    1560
ccttcactgt cgtccacttc cgcggttgcg tctgccgtca acggctccga tctttacatc    1620
cctatcaccct ggggcggtat accgaagcca gcggccgtga agccgtcga ggcgaatggg    1680
```

```
aactacctcg tcgacagctg gacggaatac ctacctgcga tccagcaggg gaggacaaca  1740
tacagcagcc agtggaactg gacgactcg catgtcatca tcactgcagc gacaatcagc  1800
gacgttcttg ctgcgggcca gacgactgtg tttacgttcg agttttatcc tcgagataac  1860
ggggttgtca acgcggtcaa ttttacgctg actgtgtaaa tacgtacaat caatccattt  1920
cgctatagtt aa                                                      1932
```

<210> SEQ ID NO 13
<211> LENGTH: 300
<212> TYPE: PRT
<213> ORGANISM: Talaromyces emersonii
<220> FEATURE:
<221> NAME/KEY: MISC_FEATURE
<222> LOCATION: (1)..(300)
<223> OTHER INFORMATION: acetyl xylan esterase

<400> SEQUENCE: 13

```
Met Ala Arg Phe Ser Ile Leu Ser Ala Ile Tyr Leu Tyr Ile Leu Leu
1               5                   10                  15

Val Gly Ser Cys Leu Ala Gln Val Pro Arg Gly Ser Leu Gln Gln Val
            20                  25                  30

Thr Asn Phe Gly Ser Asn Pro Thr Asn Val Gly Met Tyr Ile Tyr Val
        35                  40                  45

Pro Asn Asn Leu Ala Ala Lys Pro Gly Ile Val Val Ala Ile His Tyr
    50                  55                  60

Cys Thr Gly Ser Ala Gln Ala Tyr Tyr Ser Gly Thr Pro Tyr Ala Gln
65                  70                  75                  80

Leu Ala Glu Gln Tyr Gly Phe Ile Val Ile Tyr Pro Ser Ser Pro Tyr
                85                  90                  95

Ser Gly Thr Cys Trp Asp Val Ser Ser Gln Ala Ala Leu Thr His Asn
            100                 105                 110

Gly Gly Gly Asp Ser Asn Ser Ile Ala Asn Met Val Thr Trp Thr Ile
        115                 120                 125

Gln Gln Tyr Asn Ala Asp Thr Ser Lys Val Phe Val Thr Gly Ser Ser
    130                 135                 140

Ser Gly Ala Met Met Thr Asn Val Met Ala Ala Thr Tyr Pro Glu Leu
145                 150                 155                 160

Phe Ala Ala Ala Thr Val Tyr Ser Gly Val Ala Ala Gly Cys Phe Val
                165                 170                 175

Ser Ser Thr Asn Gln Val Asp Ala Trp Asn Ser Ser Cys Ala Leu Gly
            180                 185                 190

Gln Val Val Asn Thr Pro Gln Val Trp Ala Gln Val Ala Glu Asn Met
        195                 200                 205

Tyr Pro Gly Tyr Asn Gly Pro Arg Pro Arg Met Gln Ile Tyr His Gly
    210                 215                 220

Ser Ala Asp Thr Thr Leu Tyr Pro Gln Asn Tyr Tyr Glu Glu Cys Lys
225                 230                 235                 240

Gln Trp Ala Gly Val Phe Gly Tyr Asp Tyr Asn Asn Pro Gln Gln Val
                245                 250                 255

Glu Gln Asn Thr Pro Glu Ala Asn Tyr Gln Thr Thr Ile Trp Gly Pro
            260                 265                 270

Asn Leu Gln Gly Ile Tyr Ala Thr Gly Val Gly His Thr Val Pro Ile
        275                 280                 285

His Gly Gln Gln Asp Met Glu Trp Phe Gly Phe Ala
    290                 295                 300
```

<210> SEQ ID NO 14
<211> LENGTH: 903
<212> TYPE: DNA
<213> ORGANISM: Talaromyces emersonii
<220> FEATURE:
<221> NAME/KEY: misc_feature
<222> LOCATION: (1)..(903)
<223> OTHER INFORMATION: acetyl sylan esterase (coding sequence)

<400> SEQUENCE: 14

```
atggcacgct tttcaattct ttctgctatc tatctctata tccttttggt cggttcctgt     60
cttgcccagg tgcctcgtgg ctcgcttcag caggtcacca atttcgggtc caatccgacc    120
aatgtgggca tgtacattta tgtgccaaac aatctggctg cgaaaccggg gatagtcgtg    180
gccattcatt actgcactgg ttccgcgcag gcatactatt ctggcacccc gtacgcacag    240
ttggcagagc agtatggctt catcgtcatc tacccgagca gcccatacag cggcacctgc    300
tgggatgtca gctcgcaggc agccctcacc cacaacggcg gtggagacag caactcgatt    360
gccaatatgg tcacctggac gatccagcaa tataacgcgg acacgagcaa ggtctttgtg    420
acagggagca gctctggagc gatgatgacg aacgtcatgg cagccaccta ccccgagctc    480
ttcgctgcag ccaccgtcta ctcgggcgtt gcggcaggat gcttcgtttc gtccacgaac    540
caggtcgacg catggaacag cagctgcgcc ttgggccagg tcgtcaacac gccgcaggta    600
tgggcccagg tggccgaaaa catgtacccg ggctacaacg gccccgaccc cggatgcgag    660
atctaccacg gcagcgccga cacgacgctc tacccgcaga actactacga ggagtgcaag    720
cagtgggccg gcgtctttgg ctacgactac aacaaccccc agcaggttga gcagaacacg    780
cccgaggcca actatcagac cacgatctgg ggcccgaacc tgcaggggat ctacgctacg    840
ggagttggcc atacggttcc tatccatggt cagcaggaca tggagtggtt tgggtttgcg    900
tag                                                                  903
```

<210> SEQ ID NO 15
<211> LENGTH: 408
<212> TYPE: PRT
<213> ORGANISM: Talaromyces emersonii
<220> FEATURE:
<221> NAME/KEY: MISC_FEATURE
<222> LOCATION: (1)..(408)
<223> OTHER INFORMATION: xylanase

<400> SEQUENCE: 15

```
Met Val Arg Leu Ser Pro Val Leu Leu Ala Ser Ile Ala Gly Ser Gly
1               5                   10                  15

Leu Pro Leu Ala Gln Ala Ala Gly Leu Asn Thr Ala Ala Lys Ala Ile
            20                  25                  30

Gly Leu Lys Tyr Phe Gly Thr Ala Thr Asp Asn Pro Glu Leu Ser Asp
        35                  40                  45

Thr Ala Tyr Glu Thr Gln Leu Asn Asn Thr Gln Asp Phe Gly Gln Leu
    50                  55                  60

Thr Pro Ala Asn Ser Met Lys Trp Asp Ala Thr Glu Pro Glu Gln Asn
65                  70                  75                  80

Val Phe Thr Phe Ser Ala Gly Asp Gln Ile Ala Asn Leu Ala Lys Ala
                85                  90                  95

Asn Gly Gln Met Leu Arg Cys His Asn Leu Val Trp Tyr Asn Gln Leu
            100                 105                 110

Pro Ser Trp Val Thr Ser Gly Ser Trp Thr Asn Glu Thr Leu Leu Ala
        115                 120                 125
```

Ala Met Lys Asn His Ile Thr Asn Val Val Thr His Tyr Lys Gly Gln
    130                 135                 140

Cys Tyr Ala Trp Asp Val Val Asn Glu Ala Leu Asn Asp Asp Gly Thr
145                 150                 155                 160

Tyr Arg Ser Asn Val Phe Tyr Gln Tyr Ile Gly Glu Ala Tyr Ile Pro
                165                 170                 175

Ile Ala Phe Ala Thr Ala Ala Ala Asp Pro Asn Ala Lys Leu Tyr
            180                 185                 190

Tyr Asn Asp Tyr Asn Ile Glu Tyr Pro Gly Ala Lys Ala Thr Ala Ala
        195                 200                 205

Gln Asn Leu Val Lys Leu Val Gln Ser Tyr Gly Ala Arg Ile Asp Gly
210                 215                 220

Val Gly Leu Gln Ser His Phe Ile Val Gly Glu Thr Pro Ser Thr Ser
225                 230                 235                 240

Ser Gln Gln Gln Asn Met Ala Ala Phe Thr Ala Leu Gly Val Glu Val
                245                 250                 255

Ala Ile Thr Glu Leu Asp Ile Arg Met Gln Leu Pro Glu Thr Glu Ala
            260                 265                 270

Leu Leu Thr Gln Gln Ala Thr Asp Tyr Gln Ser Thr Val Gln Ala Cys
        275                 280                 285

Ala Asn Thr Lys Gly Cys Val Gly Ile Thr Val Trp Asp Trp Thr Asp
290                 295                 300

Lys Tyr Ser Trp Val Pro Ser Thr Phe Ser Gly Tyr Gly Asp Ala Cys
305                 310                 315                 320

Pro Trp Asp Ala Asn Tyr Gln Lys Lys Pro Ala Tyr Glu Gly Ile Leu
                325                 330                 335

Thr Gly Leu Gly Gln Thr Val Thr Ser Thr Thr Tyr Ile Ile Ser Pro
            340                 345                 350

Thr Thr Ser Val Gly Thr Gly Thr Thr Thr Ser Ser Gly Gly Ser Gly
        355                 360                 365

Gly Thr Thr Gly Val Ala Gln His Trp Glu Gln Cys Gly Gly Leu Gly
370                 375                 380

Trp Thr Gly Pro Thr Val Cys Ala Ser Gly Tyr Thr Cys Thr Val Ile
385                 390                 395                 400

Asn Glu Tyr Tyr Ser Gln Cys Leu
                405

<210> SEQ ID NO 16
<211> LENGTH: 1227
<212> TYPE: DNA
<213> ORGANISM: Talaromyces emersonii
<220> FEATURE:
<221> NAME/KEY: misc_feature
<222> LOCATION: (1)..(1227)
<223> OTHER INFORMATION: xylanase (coding sequence)

<400> SEQUENCE: 16
atggttcgcc tcagtccagt cttgctcgcc tccatcgcag gctctggcct gcctctagcc      60
caagcagcag gcctcaacac agccgccaaa gccatcggcc tgaaatactt tggcacagcg     120
accgacaacc ccgagctgag cgacaccgcg tacgagacga gctcaacaa cacgcaggat     180 ttcgggcagt tgacgccggc gaattcgatg aagtgggatg ccaccgagcc cgagcagaat     240
gtcttcacgt ttagcgccgg cgatcagatt gccaacttgg ccaaggcgaa tggccagatg     300
ttgcggtgtc ataatcttgt ttggtacaat cagttgccgt cgtgggtcac cagtggctcc     360

```
tggaccaacg agacgctgct tgctgccatg aagaatcaca tcaccaacgt cgttacccat    420
tacaagggcc agtgctacgc atgggatgtc gttaatgagg ccctcaacga cgacggcacc    480
taccgcagca acgtcttcta ccagtacatc ggtgaggcgt acatcccat cgccttcgcg     540 acggccgccg ccgccgaccc caacgccaag ctgtactaca acgactacaa catcgagtac    600
ccgggggcca aggcgacggc ggcgcagaac ctggtcaagc tggtgcagtc gtacggcgcg    660
cgcatcgacg gcgtcggcct gcagtcgcac ttcatcgtgg gcgagacgcc cagcaccagc    720
tcccagcagc agaacatggc cgccttcacg gcgctgggcg tcgaggtcgc catcaccgag    780
ctcgacatcc gcatgcagct gcccgagacg gaagccctgc tgacgcagca ggccaccgac    840
taccagagca ccgtgcaggc ctgcgccaac accaagggct gcgtcggcat caccgtctgg    900
gactggaccg acaagtactc gtgggtgccc agcaccttct cgggctatgg cgacgcctgt    960
ccctgggacg ccaactacca gaagaagccc gcgtacgaag gcatcctcac tgggcttgga   1020
cagacggtca ccagcaccac ctacatcatc tcgccgacga cgtctgtcgg aacgggcacg   1080
acgacctcga gcggcggaag cggcggcacg actggcgtgg cccagcattg ggagcagtgc   1140
ggtggactgg gctggactgg tccgacggtt tgcgcaagtg gctacacttg cactgtcatc   1200
aatgagtatt actcgcagtg tctgtaa                                        1227
```